United States Patent
Akhavan-Tafti et al.

(10) Patent No.: US 6,696,569 B2
(45) Date of Patent: Feb. 24, 2004

(54) COMPOUNDS FOR GENERATING CHEMILUMINESCENCE WITH A PEROXIDASE

(75) Inventors: Hashem Akhavan-Tafti, Brighton, MI (US); Zahra Arghavani, West Bloomfield, MI (US); Renuka DeSilva, Northville, MI (US)

(73) Assignee: Lumigen, Inc., Southfield, MI (US)

( * ) Notice: Subject to any disclaimer, the term of this patent is extended or adjusted under 35 U.S.C. 154(b) by 8 days.

(21) Appl. No.: 09/833,050

(22) Filed: Apr. 11, 2001

(65) Prior Publication Data

US 2001/0039345 A1 Nov. 8, 2001

Related U.S. Application Data

(63) Continuation of application No. 08/927,381, filed on Sep. 12, 1997.

(51) Int. Cl.[7] ............................................. C07D 219/00
(52) U.S. Cl. ........................ 546/102; 546/339; 549/13; 549/26; 549/388; 549/427
(58) Field of Search ................................. 546/102, 339; 549/26, 13, 388, 427

(56) References Cited

U.S. PATENT DOCUMENTS 6,126,870 A * 10/2000 Akhavan-Tafti ........ 549/102 X

* cited by examiner

*Primary Examiner*—Samuel Barts
(74) *Attorney, Agent, or Firm*—Richard S. Handley

(57) ABSTRACT

Novel compounds comprising a C—C double bond substituted at one carbon with two oxygen or sulfur atom-containing groups are disclosed. The compounds are useful in methods and compositions for generating chemiluminescence by reaction with a peroxidase enzyme and a peroxide. The chemiluminescence thus produced can be used as a detectable signal in assays for peroxidase enzymes and in assays employing enzyme-labeled specific binding pairs.

9 Claims, 12 Drawing Sheets

5000  1000  180  30  5

5000  1000  180  30  5

COMPOUNDS FOR GENERATING CHEMILUMINESCENCE WITH A PEROXIDASE

CROSS REFERENCE TO RELATED APPLICATION

This application is a continuation of applicant's co-pending application U.S. application Ser. No. 08/927,381, filed on Sep. 12, 1997.

FIELD OF THE INVENTION

The present invention relates to chemiluminescent compositions which react with a peroxidase and a peroxide to generate chemiluminescence. In particular, the present invention relates to compositions containing novel electron-rich alkenes which react with a peroxidase and a peroxide to produce an excited state carbonyl compound. The invention further relates to assay methods for detecting a peroxidase and for detecting peroxidase-labeled specific binding partners in immunoassays, nucleic acid probe assays and the like.

BACKGROUND OF THE INVENTION

Peroxidase enzymes such as horseradish peroxidase (HRP) are frequently used as markers or labels in enzyme-linked assays for biological molecules and other analytes of interest such as drugs, hormones, steroids and cancer markers. Chemiluminescent detection of these enzymes offers a safe, convenient and sensitive means to provide a quantitative measure of the amount of enzyme in a sample or of the amount of an enzyme-labeled analyte or labeled specific binding partner for an analyte. Other chemiluminescent reaction schemes have been developed to quantitate the level of particular peroxidase enzymes.

a. Chemiluminescent Peroxidase Substrates. Amino-substituted cyclic acylhydrazides such as the well-known luminol and isoluminol react with $H_2O_2$ and a peroxidase catalyst (such as horseradish peroxidase, HRP) under basic conditions with emission of light. This reaction has been used as the basis for analytical methods for the detection of $H_2O_2$ and for the peroxidase. Heterocyclic analogs of luminol such as (8-amino-5-chloro-7-phenylpyrido[3,4-d]pyridazine-1,4(2H,3H)dione (M. Ii, et al., Biochem. Biophys. Res. Comm., 193(2), 540–5 (1993)); pyridazinoquinoxalinones (U.S. Pat. No. 5,324,835) and 1,3-disubstituted pyrazolo[4',3':5',6']pyrido-[2,3-d]-pyrazinediones (Y. Tominaga, et al., Tetrahedron Lett., 36, 8641–4 (1995)) are known to react with a peroxidase and peroxide to produce chemiluminescence. Other hydrazide compounds which are chemiluminescent when oxidized by a peroxidase and a peroxide are hydroxy-substituted phthalhydrazides (U.S. Pat. No. 5,552,298).

Applicant's U.S. Pat. Nos. 5,491,072, 5,523,212 and 5,593,845 disclose chemiluminescent N-alkylacridan-carboxylic acid esters, thioesters and sulfonimides which produce light upon reaction with a peroxide and a peroxidase for use in detecting peroxidases and in assays. A PCT application (WO 94/02486) describes the chemiluminescent reaction of spiroacridan compounds with hydrogen peroxide. The reaction is enhanced by the addition of horseradish peroxidase.

Various compounds of biological origin, collectively termed luciferins, are oxidized by a peroxidase (summarized in L. J Kricka and G. H. G. Thorpe, in Luminescence Immunoassay and Molecular Applications, K. Van Dyke and R. Van Dyke, eds., CRC Press, Boca Raton, 1990, pp. 77–98). In some instances, hydrogen peroxide is not utilized in which case the enzyme is functioning as an oxidase.

Certain phenol compounds produce chemiluminescence on oxidation with a peroxidase. As examples, pyrogallol B-1 and purpurogallin B-2 are cited in Kricka and Thorpe, ibid. as well as the coumarin-type compounds coumarin, umbelliferone and esculin (D. Slawinska, J. Slowinski, J. Biolumin. Chemilumin., 4, 226–30 (1989)); phloroglucinol B-3 (M. Halmann, et al., Photochem. Photobiol., 30, 165–7 (1979)); and acetaminophen B-4 (K. Schmitt, G. Cilento, Photochem. Photobiol., 51, 719–23 (1990)).

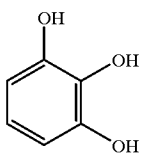

B-1

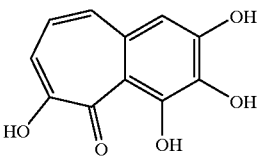

B-2

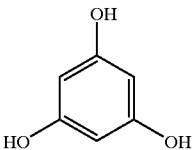

B-3

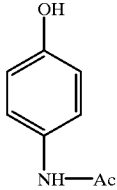

B-4

Other miscellaneous compounds reported to produce weak chemiluminescence in the presence of a oxygen or peroxide and a peroxidase are a synthetic Schiff base-containing polymer ((R. Zoulik, et al., Coll. Czech. Chem. Commun., 60, 95–103 (1995)); indole-3-acetic acid in the presence of xanthene dyes with or without hydrogen peroxide (S. Krylov, A. Chebotareva, FEBS, 324(1), 6–8 (1993); tyrosine, tryptophan and chlorpromazine (M. Nakano, J. Biolumin. Chemilumin. 4, 231–40 (1989)) and MCLA B-8 M. (Mitani, et al., J. Biolumin. Chemilumin. 9, 355–61 (1994)) which have the respective structures B-5–B-8 as shown below.

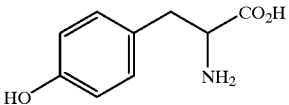

B-5

-continued

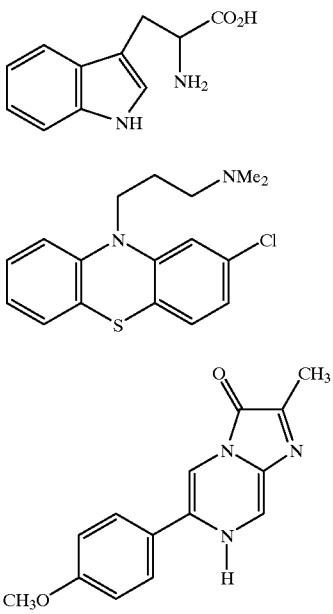

None of the foregoing references disclose the chemiluminescent oxidation of the presently disclosed compounds by a peroxidase b. Reaction of Enols with HRP. A series of papers describe the peroxidase-catalyzed air oxidation of enolizable aldehydes (H. Gallardo, et al., Biochim. Biophys. Acta, 789, 57–62 (1984); W. J. Baader, et al., Biochem. Ed., 14(4), 190–2 (1986); I. Nantes, et al., Photochem. Photobiol., 63(6), 702–8 (1996)). The reactive substrate is thought to be the small quantity of the enol form in equilibrium with the aldehyde. The reaction of the aldehyde is catalyzed by enol phosphates, but the enol phosphate itself is not consumed. The reference teaches that the enol phosphate does not react with a peroxidase to produce chemiluminescence. Energy transfer to fluorescent energy acceptors increased light emission (M. T. Grijalba, et al., Photochem. Photobiol., 63(6), 697–701 (1996)). Aldehydes masked as enol silyl ethers (Baader, ibid.) or enol acetates were used in coupled assays in which the enol was unmasked in a first step to generate an enol in situ which subsequently reacted with a peroxidase to generate chemiluminescence (A. Campa, et al., Photochem. Photobiol., 63(6), 742–5 (1996)).

c. Peroxidase Enhancers. Numerous enhancers have been employed in order to increase the quantity and duration of chemiluminescence from the reaction of a peroxidases with known chemiluminescent substrates including the aforementioned luminol and the acridancarboxylic acid derivatives. These include benzothiazole derivatives such as D-luciferin, various phenolic compounds such as p-iodophenol, p-phenylphenol, naphthols and aromatic amines as listed in G. Thorpe, L. Kricka, in *Bioluminescence and Chemiluminescence, New Perspectives*, J. Scholmerich, et al, Eds., pp. 199–208 (1987). Other compounds which function as enhancers of the chemiluminescent oxidation of amino-substituted cyclic acylhydrazides by a peroxidase include 4-(4-hydroxyphenyl)-thiazole (M. Ii, ibid.), a group of compounds disclosed in U.S. Pat. No. 5,171,668, 2-hydroxy-9-fluorenone, and a group of hydroxy-substituted benzoxazole derivatives as disclosed in U.S. Pat. No. 5,206, 149 and certain phenylboronic acid compounds as described in U.S. Pat. No. 5,629,168. None of the foregoing references disclose the chemiluminescent oxidation of the present compounds by a peroxidase alone or with the use of enhancers.

d. Enhancement of Chemiluminescent Peroxidase Reactions by Surfactants. Enhancement of the chemiluminescence produced in peroxidase-catalyzed reactions using polymeric and monomeric surfactants is known in the art. Enhancement can occur by affecting the outcome of one or more steps e.g. by increasing the fluorescence quantum yield of the emitter, by increasing the percentage of product molecules produced in the excited state, by increasing the fraction of molecules undergoing the chemiluminescent reaction through inhibition of competing side reactions or by promoting the action of an enzyme catalyst. No clear or consistent pattern exists concerning the effect of polymeric and monomeric surfactants on chemiluminescent reactions. It is impossible to predict which surfactant compounds, if any, may enhance the chemiluminescence from a particular process and can only be determined by substantial experimentation.

The cationic polymeric surfactant poly-N-ethyl-4-vinylpyridinium bromide completely inhibited the chemiluminescent reaction of luminol by a negatively charged insulin-peroxidase conjugate and diminished chemiluminescence to a lesser extent when the native enzyme was used (S. B. Vlasenko, et al., *J. Biolumin. Chemilumin.*, 4, 164–176 (1989)).

A published Japanese Patent Application No. JP 06,242, 111 and a paper (R. Iwata, et al., Anal. Biochem., 231, 170–4 (1995)) disclose the use of nonionic surfactant and skim milk in the chemiluminescent peroxidation of luminol to lower background emission or enhance signal/noise.

None of the foregoing references disclose the chemiluminescent oxidation of the present compounds by a peroxidase or chemiluminescence enhancement with surfactants.

d. Assays using HRP. The enzyme horseradish peroxidase has found widespread use in enzyme immunoassays and DNA hybridization assays with chemiluminescent detection using luminol or isoluminol as substrate. Commercially available kits using HRP conjugates and enhanced luminol chemiluminescent detection are available. Chemiluminescent peroxidase assays are also disclosed in the aforementioned U.S. Pat. Nos. 5,491,072, 5,523,212 and 5,593,845. No references disclose the chemiluminescent peroxidase assays using the present compounds as the substrates.

SUMMARY OF THE INVENTION

It is an object of the present invention to provide compositions containing compounds which react with a peroxidase and a peroxide to provide chemiluminescence.

It is another object of the present invention to provide compositions containing compounds which react with a peroxidase and a peroxide to provide chemiluminescence for detection of the peroxidase.

It is also an object of the present invention to provide compositions containing compounds of formula I containing a carbon-carbon double bond substituted at one terminus of the double bond with two atoms selected from oxygen or sulfur each attached to another group X or $R^1$ and substituted at the other terminus of the double bond with two groups $A^1$ and $A^2$ selected so that an excited state product $A^1A^2C=O^*$ results upon reaction of I with a peroxidase and a peroxide.

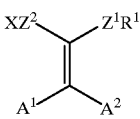

It is a further object of the present invention to provide compositions containing compounds of formula I wherein $A^1$ and $A^2$ together with the carbon atom to which they are bonded form a heterocyclic or carbocyclic ring. In particular the ring can be a nitrogen, sulfur or oxygen-containing heterocyclic ring group.

It is a further object of the present invention to provide compositions containing compounds of formula I wherein when $Z^2$ is O the group attached to the oxygen atom is part of an alkoxy group, an aryloxy group, an aralkyloxy group, a phosphate mono-, di- or triester group, a carboxyl ester group, a sulfate group, a sugar group or a silyl ether group and when $Z^2$ is S the group attached to the sulfur atom is part of the equivalent thio groups.

It is a further object of the present invention to provide methods for generating chemiluminescence upon reaction with a peroxidase and a peroxide employing the present compositions.

Still further, it is an object of the present invention to provide a method and compositions for enhancing the chemiluminescence produced on reaction of compounds of the present invention with a peroxidase.

It is yet another object of the present invention to provide chemiluminescent compositions and methods for use in detecting peroxidases and conjugates in immunoassays, nucleic acid probe assays, western blot assays, Southern blot assays and other assays by generally known methods which employ enzyme labels for detection of analytes. The assays are thus useful for detecting analytes in such assays by detecting the peroxidase or conjugate and relating the chemiluminescence produced thereby to the presence or amount of the analyte.

DESCRIPTION OF THE PREFERRED EMBODIMENTS

Definitions

Figure 1:
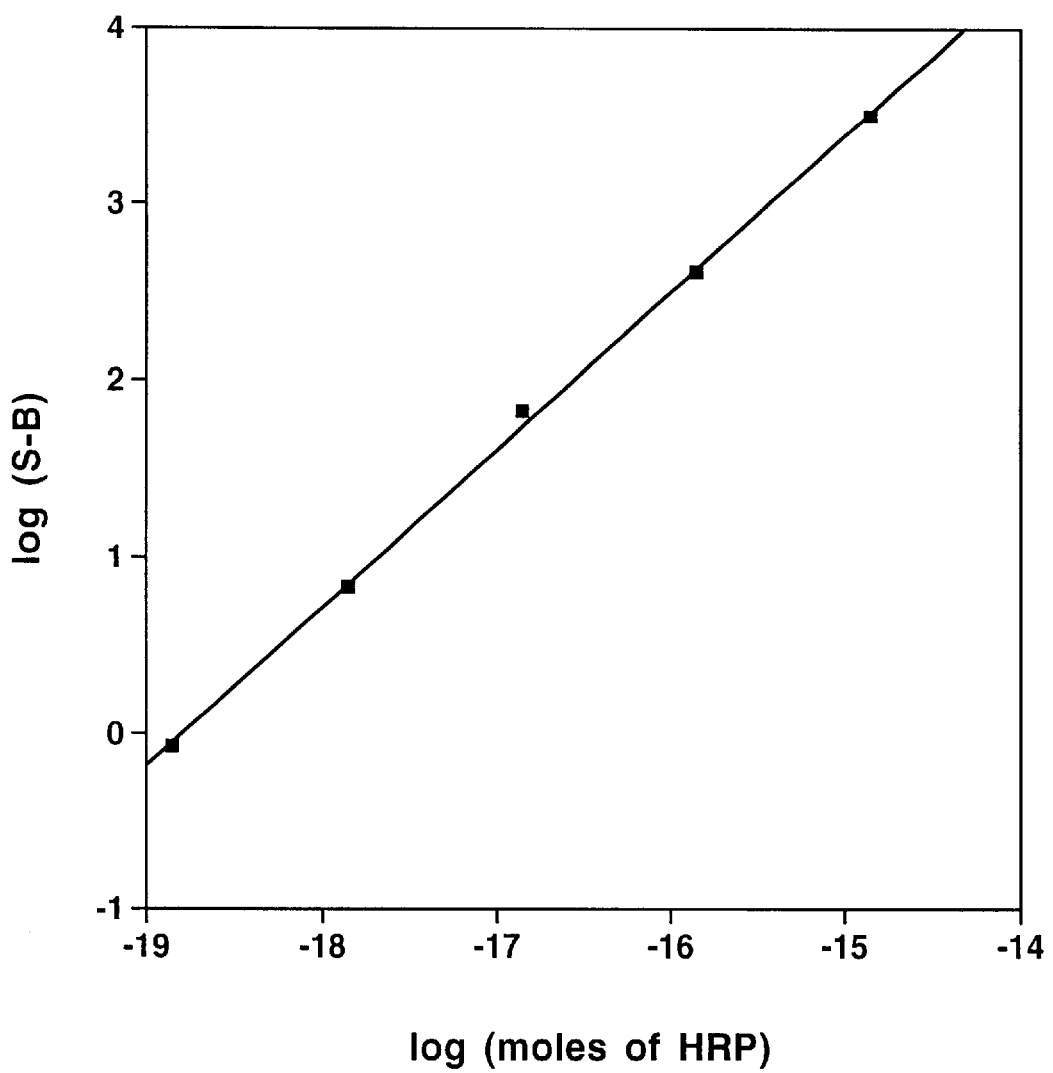
FIG. 1 is a graph relating the amount of HRP to the chemiluminescence intensity at 15 min emitted by 100 μL of a reagent described in Example 20 containing acridan phosphate 5 triggered at room temperature. Chemiluminescence emission was initiated by addition of 10 μL of solutions of HRP containing between $1.4 \times 10^{-15}$ and $1.4 \times 10^{-19}$ moles of enzyme to 100 μL of the reagent comprising 0.055 M tris buffer, pH 8.6, 0.25 mM urea peroxide, 0.05 mM p-phenylphenol, 0.5 mM EDTA, 0.0125% Tween 20 and $3.3 \times 10^{-4}$ M acridan 5 in the wells of a black microplate. The term S-B refers to the chemiluminescence signal (S) in Relative Light Units (RLU) in the presence of HRP corrected for background chemiluminescence (B) in the absence of HRP.

Alkyl—A branched, straight chain or cyclic hydrocarbon group containing from 1–20 carbons. Lower alkyl as used herein refers to those alkyl groups containing up to 8 carbons.

Alkenyl—A branched, straight chain or cyclic hydrocarbon group containing at least one C—C double bond and containing from 2–20 carbons. Lower alkenyl as used herein refers to those alkenyl groups containing up to 8 carbons.

Alkynyl—A branched or straight chain hydrocarbon group containing at least one C—C triple bond and containing from 2–20 carbons. Lower alkynyl as used herein refers to those alkynyl groups containing up to 8 carbons.

Analyte—A substance the presence or amount of which is to be measured in a sample by an assay. Analytes include organic and biological molecules to which a specific binding partner having a specific binding affinity exists. Exemplary analytes include, without limitation, single stranded or double stranded DNA, RNA, DNA-RNA complexes, oligonucleotides, antibodies, antibody fragments, antibody-DNA chimeras, antigens, haptens, proteins, lectins, avidin, streptavidin and biotin. Other exemplary analytes also include hydrolytic enzymes, inhibitors of hydrolytic enzymes and dihydroxyaromatic compounds.

Aryl—An aromatic ring-containing group containing 1 to 5 carbocyclic aromatic rings, which can be substituted with 1 or more substituents other than H.

Biomedical analysis—Analyses of samples of biological origin for analytes of interest. The analyses can be immunoassays, western blots, northern blots, Southern blots, DNA hybridization assays, DNA sequence analysis, colony hybridizations, gene expression analysis, high throughput drug screening, detection of infectious agents or pathogens and the like.

Glycosyl—Residues of carbohydrate groups including hexoses and pentoses and contain one or more sugar unit. Examples include fructose, galactose, glucose, glucuronate, mannose, ribose, N-acetylglucosamine and the like.

Halogen—Fluorine, chlorine, bromine or iodine atoms.

Heteroaryl—An aromatic ring-containing group containing 1 to 5 carbocyclic aromatic rings in which at least one of the ring carbon atoms is replaced with a nitrogen, oxygen or sulfur atom and which can be substituted with 1 or more substituents other than H.

Luminescent—capable of emitting light when excited to an electronic excited state. The light can be emitted either as fluorescence when decaying from a singlet excited state or as phosphorescence when decaying from a triplet excited state.

Peroxide—A compound containing an O—O bond, preferably hydrogen peroxide or a complex of hydrogen peroxide such as urea peroxide, perborate or percarbonate.

Alkyl

Sample—A fluid containing or suspected of containing one or more analytes to be assayed. Typical samples which are analyzed by the chemiluminescent reaction method are biological samples including body fluids such as blood, plasma, serum, urine, semen, saliva, cell lysates, tissue extracts and the like. Other types of samples include food samples and environmental samples such as soil or water.

Specific binding pair—Two substances which exhibit a mutual binding affinity. Examples include antigen-antibody, hapten-antibody or antibody-antibody pairs, complementary oligonucleotides or polynucleotides, avidin-biotin, streptavidin-biotin, hormone-receptor, lectin-carbohydrate, IgG-protein A, nucleic acid-nucleic acid binding protein and nucleic acid-anti-nucleic acid antibody.

Substituted—Refers to the replacement of at least one hydrogen atom on a group by a non-hydrogen group. It should be noted that in references to substituted groups it is intended that multiple points of substitution can be present unless clearly indicated otherwise.

It has been unexpectedly discovered that compounds of formula I below react with a peroxide and a peroxidase to generate chemiluminescence. Compounds of the present invention which produce chemiluminescence in the presence of a peroxidase comprise a carbon-carbon double bond substituted at one terminus of the double bond with two atoms selected from oxygen and sulfur atoms and have the formula I:

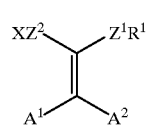

I wherein $Z^1$ and $Z^2$ are independently selected from O and S atoms, $R^1$ is an organic group containing from 1 to about 50 non-hydrogen atoms, X is a group containing from 1 to about 50 non-hydrogen atoms and $A^1$ and $A^2$ are groups selected so that an electronic excited state product $A^1A^2C=O^*$ results upon reaction of I with a peroxidase according to the reaction below.

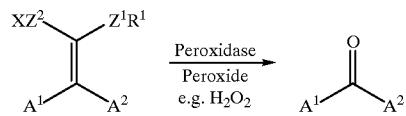

The groups $A^1$, $A^2$, $Z^1$, $Z^2$, X and $R^1$ are selected so that the resulting compound I will have an electron-rich C—C double bond. In general, most compounds of general formula I having $Z^1$ and $Z^2$ selected from O and S atoms have a sufficiently electron-rich C—C double bond. Compounds in which $A^1$ and/or $A^2$ are strongly electron-withdrawing groups may not function and are not preferred.

The group $R^1$ can be any organic group containing from 1 to about 50 non-hydrogen atoms selected from C, N, O, S, P, Si and halogen atoms which allows light production. By the latter is meant that when a compound of formula I is reacted with a peroxidase and a peroxide the light is produced and can involve the production of one or more chemiluminescent intermediates. Groups which can function as the $R^1$ group include, without limitation, alkyl, substituted alkyl, aryl, substituted aryl, aralkyl and substituted aralkyl groups. Substituent groups other than H atoms, such as ionic groups or polar groups, can be incorporated in various numbers and at selected positions on the carbon chain or ring of $R^1$ in order to modify the properties of the compound or to provide for convenience of synthesis. Such properties include, for example, chemiluminescence quantum yield, rate of reaction with the enzyme, maximum intensity of light emission, duration of light emission, wavelength of light emission, solubility in the reaction medium. One or more groups which permit covalent coupling to another molecule such as s specific binding partner can also be included as substituents on $R^1$. Exemplary specific substituents and their effects are illustrated in the specific examples below, which, however, do not limit the scope of the invention.

The group X is selected from substituted or unsubstituted alkyl, substituted or unsubstituted aryl, substituted or unsubstituted aralkyl groups of 1–20 carbon atoms, substituted or unsubstituted alkyl or aryl carbonyl groups having from 1–20 carbon atoms, tri($C_1$–$C_8$ alkyl)silyl groups, an $SO_3^-$ group, glycosyl groups and phosphoryl groups of the formula PO(OR')(OR") wherein R' and R" are independently selected from substituted or unsubstituted alkyl, substituted or unsubstituted aryl and substituted or unsubstituted aralkyl groups of 1–20 carbon atoms, trialkylsilyl groups, alkali metal cations, alkaline earth cations, ammonium and phosphonium cations. Substituted alkyl groups will contain at least one group other than a hydrogen atom, such as ionic groups or polar groups, and can be incorporated at selected positions on the carbon chain or ring of R' or R" in order to modify the properties of compound I or to provide for convenience of synthesis. Exemplary substituted alkyl groups include a cyanoethyl group or a trimethylsilylethyl group.

The groups $A^1$ and $A^2$ are independently selected from hydrogen or organic groups which upon reaction of compound I with peroxide and a peroxidase form an electronic excited state product $A^1A^2C=O^*$ including, without limitation, hydrogen, alkyl, substituted alkyl, aryl, substituted aryl, aralkyl and substituted aralkyl groups, heteroaryl, substituted heteroaryl, alkenyl, alkynyl, alkoxy, aryloxy, alkylamino, arylamino, alkylthio and arylthio groups provided that at least one is not hydrogen. The groups $A^1$ and $A^2$ can be joined together to form a heterocyclic or carbocyclic ring which includes the carbon atom separating $A^1$ and $A^2$. In general the groups $A^1$ and $A^2$ will contain from 1–50 non-hydrogen atoms selected from C, N, O, S, P and halogens and more usually from 1–20 non-hydrogen atoms.

In a first group of preferred compounds of formula I, one of $A^1$ and $A^2$ is a substituted or unsubstituted aryl group and the other is selected from alkyl, substituted alkyl, aryl, substituted aryl, aralkyl, substituted aralkyl, heteroaryl, substituted heteroaryl, alkenyl, alkynyl, alkoxy, aryloxy, alkylamino, arylamino, alkylthio and arylthio. Preferably at least one of the aryl groups is substituted with at least one group selected from amino, alkylamino, dialkylamino and OY' where Y' is hydrogen or an alkali metal ion. The aryl group comprises 1–4 fused carbocyclic or heterocyclic 5 or 6-membered rings. When one or more of the rings is a heterocyclic ring, the heteroatoms in the ring are selected from N, O and S atoms. Preferred aryl groups are phenyl, naphthyl, anthryl and pyrenyl any of which can be substituted with non-hydrogen substituents. More preferred are phenyl and naphthyl groups.

Particular embodiments of compounds of formula I which are reactive according to the methods of the present invention to produce chemiluminescence include as examples compounds having the structures:

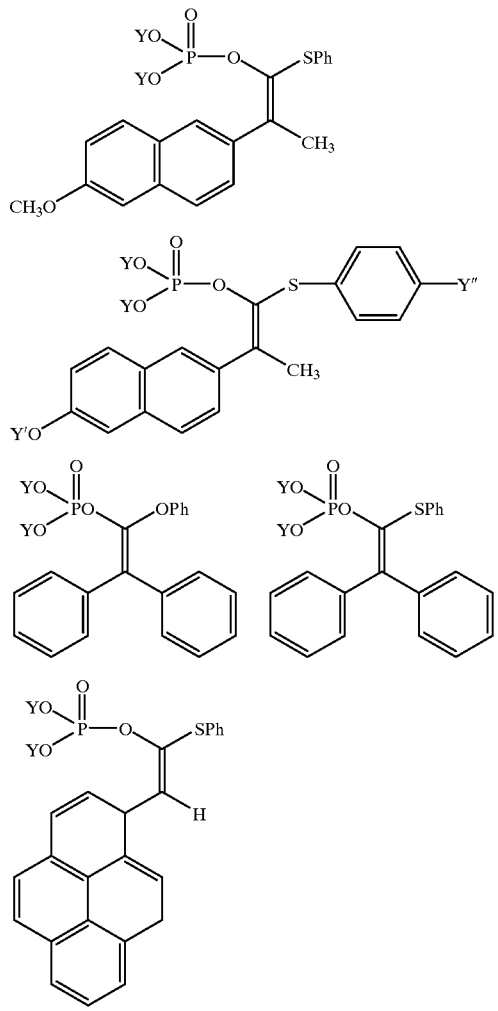

wherein Y is hydrogen, an alkali metal ion or a substituted or unsubstituted alkyl, substituted or unsubstituted aryl, substituted or unsubstituted aralkyl or trialkylsilyl group, Y' is an alkali metal ion, an alkyl carboxy ester, aryl carboxy ester, substituted or unsubstituted alkyl, substituted or unsubstituted aryl, substituted or unsubstituted aralkyl group or trialkylsilyl group and Y" is hydrogen or halogen, in particular a chlorine atom. Although only one double bond isomer is depicted for these structures it is realized that either isomer or mixtures of the two can be used in the present methods. Other structures subject to the limitations described above will occur to one of skill in the art as being useful in the methods of the present invention.

A second group of preferred compounds have formula II wherein $A^1$ and $A^2$ are joined together to form a heterocyclic ring designated Het. The heterocyclic ring system comprises at least one five or six-membered ring which contains at least one heteroatom selected from N, 0 and S atoms. The groups $X^1$, $Z^2$, X and $R^1$ are as defined above.

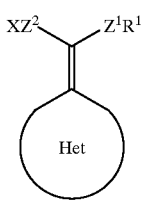

II

The heterocyclic ring system contains at least one heteroatom selected from N, O and S atoms which is in conjugation with the ring carbon bearing the exocyclic double bond. Preferred heterocyclic compounds include compounds of formulas III and IV as well as their double bond isomers or mixtures of the isomers where Q is selected from $NR^6$, O and S, Z and $R^1$ are as defined above and $R^2$–$R^6$ are defined below.

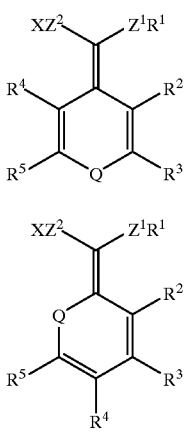

III

IV

Referring back to formula II, exemplary ring structures which can comprise the group Het include the structures below where the asterisk denotes the position of the exocyclic double bond. Without explicitly showing all possible substitution patterns, it is to be understood that in such exemplary ring structures each ring position can contain substituents other than hydrogen. Other heterocyclic ring compounds useful in the practice of the presently described methods not specifically listed below but still falling within the scope of formula II will be apparent to the skilled artisan.

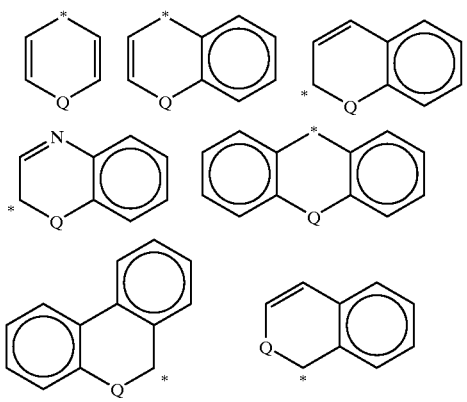

-continued

In all of the above compounds of formula III and IV, the groups $R^2$–$R^5$ each are independently H or a substituent group which permits the light to be produced and generally contain from 1 to 50 atoms selected from C, N, O, S, P and halogen atoms. Representative substituent groups which can be present include, without limitation, alkyl, substituted alkyl, aryl, substituted aryl, aralkyl, alkenyl, alkynyl, alkoxy, aryloxy, halogen, amino, substituted amino, carboxyl, carboalkoxy, carboxamide, cyano, and sulfonate groups. Either or both pairs of adjacent groups, i.e. $R^2$–$R^3$ or $R^4$–$R^5$, can be joined together to form a carbocyclic or heterocyclic ring system comprising at least one 5 or 6-membered ring which is fused to the ring bearing the exocyclic double bond. Such fused heterocyclic rings can contain N, O or S atoms and can contain ring substitutents other than H such as those mentioned above.

In all of the above compounds, the group $R^6$ is an organic group containing from 1 to 50 atoms non-hydrogen atoms selected from C, N, O, S, P and halogen atoms in addition to the necessary number of H atoms required satisfy the valencies of the atoms in the group. More preferably $R^6$ contains from 1 to 20 non-hydrogen atoms. The organic group is preferably selected from the group consisting of alkyl, substituted alkyl, aryl, substituted aryl and aralkyl groups. More preferred groups for $R^6$ include substituted or unsubstituted $C_1$–$C_4$ alkyl groups, substituted or unsubstituted benzyl groups, alkoxyalkyl and carboxyalkyl groups.

Substituent groups can be incorporated in various quantities and at selected ring or chain positions in the heterocyclic ring in order to modify the properties of the compound or to provide for convenience of synthesis of the final phosphate compound. Such properties include, e.g. chemiluminescence quantum yield, rate of reaction with the enzyme, maximum light intensity, duration of light emission, wavelength of light emission and solubility in the reaction medium. Specific substituents and their effects are illustrated in the specific examples below, which, however, are not to be considered limiting the scope of the invention in any way.

A preferred class of compounds have the formula V below wherein $R^1$ is an aryl ring group containing at least one carbocyclic or heterocyclic aromatic ring and which can be further substituted or a substituted or unsubstituted alkyl group, $Z^1$ is selected from O and S atoms and X and $R^6$ are as defined above.

V

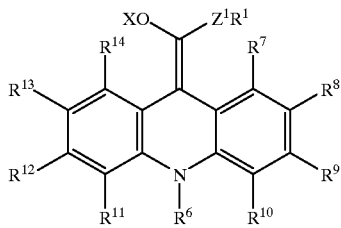

The groups $R^7$ to $R^{14}$ which can be the same or different, each are a substituent which can contain from 1 to 50 atoms selected from C, H, N, O, S, P and halogen atoms and which permit the light to be produced and can include, without limitation, alkyl, substituted alkyl, aryl, substituted aryl, aralkyl, alkenyl, alkynyl, alkoxy, aryloxy, halogen, amino, substituted amino groups, carboxyl, carboalkoxy, carboxamide, cyano, and sulfonate groups. It is preferred that $R^7$ to $R^{14}$ are selected from hydrogen, halogen and alkoxy groups such as methoxy, ethoxy, t-butoxy and the like. A preferred group of compounds has one of $R^8$, $R^9$, $R^{12}$ or $R^{13}$ as a chlorine and the other of $R^7$ to $R^{14}$ are hydrogen atoms. More preferred are compounds having the formula VI where Z and $R^1$ are as defined above, X is a phosphoryl group —PO(OR')(OR") wherein R' and R" are independently selected from substituted or unsubstituted alkyl, substituted or unsubstituted aryl and substituted or unsubstituted aralkyl groups of 1–20 carbon atoms, trialkylsilyl groups, alkali metal cations, alkaline earth cations, ammonium and phosphonium cations.

VI

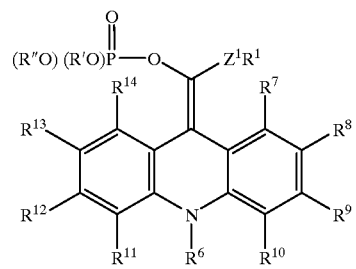

Preferably at least one of R' and R" is an alkali metal cation and more preferably both are. Among the alkali metals, lithium, sodium and potassium are preferred.

Compounds of formula I can be prepared by various methods. In a preferred method, when $Z^2$ groups is O and $Z^1$ is O or S, compound I can be prepared by reacting the enolate of an ester or thioester with a reagent of the formula X-LG where LG represents a leaving group according to the scheme below.

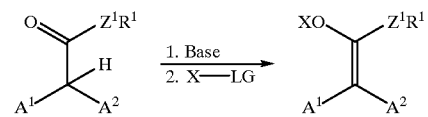

Typical leaving groups include halogens, such as chloride, bromide and iodide, sulfonates such as methanesulfonate and p-toluenesulfonate and trifluoromethanesulfonate, carboxylates such as acetate and benzoate particularly when X is an acyl group in which case X-LG would be an acid anhydride, sulfates such as methosulfate, and other groups such as imidazole, triazole and tetrazole, maleimide, succinimidoxy groups.

Methods of preparing compounds of formula I where both Z groups are S atoms include nucleophilic addition of a lithiosilane compound or a phosphorus ylide to a suitable carbonyl compound according to the two schemes below (F. A. Carey, A. S. Court, J. Org. Chem., 37, 1926–29, (1972)).

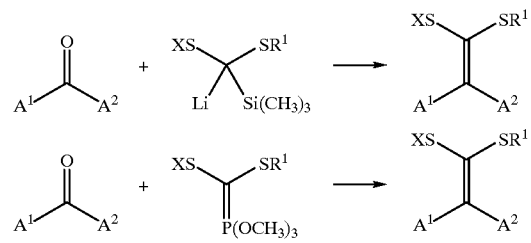

In another method, an ester is converted to a ketenedithioacetal by reaction with a bis(dialkylaluminum)-dithiol reagent as disclosed in E. J. Corey and A. P. Kozikowski, Tetrahedron Lett., 925–8 (1975) and shown below.

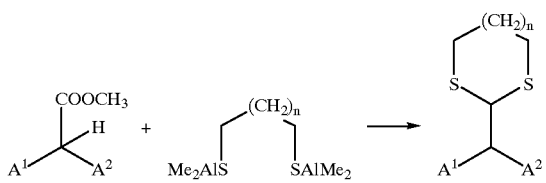

In yet another method, an anion of an active methylene group is reacted with $CS_2$ and the dithiocarboxylate is reacted with a reagent $R_1$-LG containing the $R_1$ group to form a dithioester. An example of the latter methodology is disclosed in I. Shahak and Y. Sasson, Tetrahedron Lett., 4207–10 (1973). The dithioester is converted to the enolate and reacted with a reagent of the formula X-LG.

Another aspect of the present invention is the use of compounds of any of formulas I-VI in a method to produce chemiluminescence by reaction with a peroxidase. Reaction of a compound of formula I-VI with a peroxidase and a peroxide in an aqueous buffer solution produces easily detected chemiluminescence. Light intensity reaches a maximum level within minutes at room temperature when the reaction is conducted at alkaline pH. The reaction is conducted optionally in the presence of an enhancer.

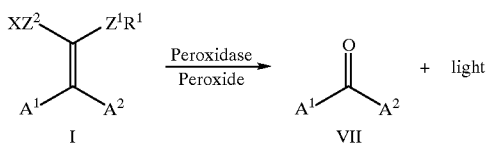

While we do not wish to put forth a specific mechanistic explanation for this discovery at this point, it is believed that the light is emitted from the electronically excited state of VII. A necessary condition for the production of light is that the reaction produces sufficient energy to form the excited state of VII. If VII* is luminescent, then chemiluminescence is produced from the reaction via emission from the excited state of VII. If composition VII* is not significantly luminescent, then chemiluminescence can be produced by the inclusion of a luminescent energy acceptor.

In a preferred method of producing chemiluminescence, compound I is reacted with a peroxidase, a peroxide and an enhancer in an alkaline buffer with a pH between about 8 and 10 to produce a continuous chemiluminescence signal which commences upon reaction of the enzyme and the compound I. Analytical sensitivity can be increased by incorporation of a non-ionic surfactant as will be described in more detail below.

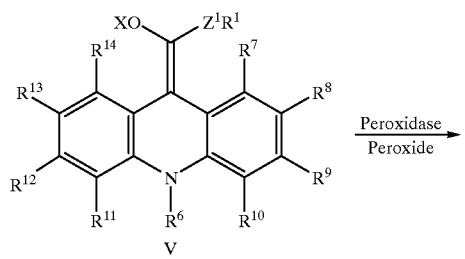

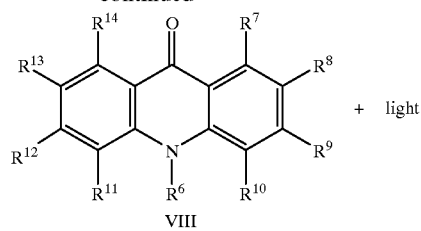

In a preferred method of producing light from the reaction of compound V with a peroxidase, the reaction is performed at a temperature between 5° C. and 50° C., preferably between 20° C. and 40° C. in an aqueous buffer solution at a pH between 7 and 10.5, preferably between 8.5 and 10. Compound V is used at a concentration between 1 $\mu$M and 20 mM, preferably between 10 $\mu$M and 1 mM. The enzyme can be a free peroxidase or a peroxidase conjugate. Light is emitted from the excited state of VIII.

Compounds of the present invention typically produce light over a 100–200 nm wide band of emission, which exhibits a maximum intensity at wavelengths in the near ultraviolet to the visible region of the electromagnetic spectrum. Typical wavelengths of maximum intensity $\lambda_{max}$ in the range of 350–500 nm. It is contemplated that compounds of formula I bearing a covalently linked fluorophore could undergo intramolecular energy transfer resulting in emission at longer wavelengths from the excited state of the fluorophore.

More than one compound of formula I can be used concurrently in a method for producing light by the action of a peroxidase. It can be advantageous in some instances to simultaneously react two or more compounds of formula I with the peroxidase. When the two or more compounds have differing luminescent or physical properties, the combination of the two may be desirable to produce a light emitting reaction with characteristics not readily achievable through the use of any one compound. Examples of luminescent and physical properties which can differ between compounds I include emission spectrum, duration of light emission, enzyme turnover, rate of rise of emission to maximum, hydrophobicity/hydrophilicity and solubility.

The peroxide component is any peroxide or alkyl hydroperoxide capable of reacting with the peroxidase. Preferred peroxides include hydrogen peroxide, urea peroxide, and perborate salts.

The peroxidase which can undergo the chemiluminescent reaction include lactoperoxidase, microperoxidase, myeloperoxidase, haloperoxidase, e.g. vanadium bromoperoxidase, horseradish peroxidase, fungal peroxidases such as lignin peroxidase and peroxidase from Arthromyces ramosus and Mn-dependent peroxidase produced in white rot fungi, and soybean peroxidase. Other peroxidase mimetic compounds which are not enzymes but possess peroxidase-like activity including iron complexes and Mn-TPPS$_4$ (Y. -X. Ci, et al., Mikrochem. J., 52, 257–62 (1995)) are known which catalyze the chemiluminescent oxidation of luminol are explicitly considered to be within the scope of the meaning of peroxidase as used herein. Conjugates or complexes of a peroxidase and a biological molecule can also be used in the method for producing chemiluminescence, the only proviso being that the conjugate display peroxidase activity. Biological molecules which can be conjugated to one or more molecules of a peroxidase include DNA, RNA, oligonucleotides, antibodies, antibody fragments, antibody-DNA chimeras, antigens, haptens, proteins, lectins, avidin, streptavidin and biotin. Complexes including or incorporating a peroxidase such as liposomes, micelles, vesicles and polymers which are functionalized for attachment to biological molecules can also be used in the methods of the present invention.

Incorporation of certain enhancer compounds into the reaction mixture promotes the reactivity of the enzyme. Included among these enhancers are phenolic compounds and aromatic amines known to enhance other peroxidase reactions as described in G. Thorpe, L. Kricka, in *Bioluminescence and Chemiluminescence, New Perspectives*, J. Scholmerich, et al, Eds., pp. 199–208 (1987), M. Ii, H. Yoshida, Y. Aramaki, H. Masuya, T. Hada, M. Terada, M. Hatanaka, Y. Ichimori, *Biochem. Biophys. Res. Comm.*, 193(2), 540–5 (1993), and in U.S. Pat. Nos. 5,171,668 and 5,206,149 which are incorporated herein by reference. Substituted and unsubstituted arylboronic acid compounds and their ester and anhydride derivatives as disclosed in U.S. Pat. No. 5,512,451 and incorporated herein by reference are also considered to be within the scope of enhancers useful in the present invention. Preferred enhancers include but are not limited to: p-phenylphenol, p-iodophenol, p-bromophenol, p-hydroxycinnamic acid, p-imidazolylphenol, acetaminophen, 2,4-dichlorophenol, 2-naphthol and 6-bromo-2-naphthol. Mixtures of more than one enhancer from those classes mentioned above can also be employed.

The use of nonionic surfactants as additives in the present chemiluminescent reactions is advantageous. Incorporation of nonionic surfactants into reactions for producing chemiluminescence by the use of a peroxidase leads to an improvement in analytical sensitivity with respect to the peroxidase by extending the duration of chemiluminescence. Nonionic surfactants useful in the practice of the present invention include by way of example polyoxyethylenated alkylphenols, polyoxyethylenated alcohols, polyoxyethylenated ethers and polyoxyethylenated sorbitol esters.

Cationic surfactants, including quaternary ammonium salt compounds such as CTAB, are advantageous for use in increasing the level of chemiluminescence emitted when certain compounds of the present invention are reacted with a peroxidase and a peroxide. For example, light intensity from the reaction of compound 43 or 46 shown below according to the present invention was increased more than ten-fold when CTAB was included in the reaction mixture.

The reaction of the present invention is carried out in solution such as an aqueous buffer which may be in contact with the surface of a solid support such as a bead, tube, membrane or microwell plate coated with peroxidase. Suitable buffers include any of the commonly used buffers capable of maintaining a pH in the range of about 6 to about 9 for example, phosphate, borate, carbonate, tris (hydroxymethyl-amino)methane, glycine, tricine, 2-amino-2-methyl-1-pro-panol, diethanolamine and the like. The preferred method of practicing the invention in this regard is determined by the requirements of the particular intended use.

Light emitted by the present method can be detected by any suitable known means such as a luminometer, x-ray film, high speed photographic film, a CCD camera, a scintillation counter, a chemical actinometer or visually. Each detection means has a different spectral sensitivity. The human eye is optimally sensitive to green light, CCD cameras display maximum sensitivity to red light, x-ray films with maximum response to either UV to blue light or green light are available. Choice of the detection device will be governed by the application and considerations of cost, convenience, and whether creation of a permanent record is required.

In a further embodiment, luminescent energy acceptors can be employed to shift the maximum emission to longer wavelengths (red-shifting) and/or to increase the quantity of luminescence emitted. Various techniques for red-shifting emission are known in the art of chemiluminescent reactions and assays. Covalently linked fluorophores as described above are one example. Fluorescers can alternatively be added to the reaction solution as separate species. Fluorescers can be linked to a polymer or associated with a micelle or polymer in order to bring the fluorescer in close contact to the compound. Fluorescent energy-transfer agents can be employed to advantage when the inherent fluorescence efficiency of the donor excited reaction product $A^1A^2C{=}O^*$ is low or when the excited reaction product is a triplet excited state. In the first case energy transfer may be of the singlet-singlet type, in the latter case it may be of the triplet-singlet type. Suitable energy transfer agents have an excited state at an energy level which overlaps that of the excited reaction product $A^1A^2C{=}O^*$ to permit the transfer of excitation energy and a fluorescent excited state which may or may not be the same as the excited state which overlaps that of the donor. Energy transfer agents useful for effecting singlet-singlet energy transfer are well known in the art. Energy transfer agents useful for effecting triplet-singlet energy transfer are also known in the art and usually possess at least one metal atom or other heavy atoms such as bromine or iodine atoms. Typical examples are 9,10-dibromoanthracene (DBA), sulfonated derivatives of DBA and $Ru(bpy)_3^{2+}$. Fluorescent energy transfer agents are evaluated empirically by comparing the intensity or wavelength of chemiluminescence produced in a reaction of a peroxidase, a peroxide and a compound of formula I in the presence and absence of the agent.

An important use of the present chemiluminescent methods is for detecting the presence or amount of an analyte in an assay procedure by a chemiluminescent reaction. The method comprises the steps of contacting a sample suspected of containing the analyte with a chemiluminescent compound of the present invention and a peroxidase, detecting the light produced in a qualitative method and, if quantitation is desired, relating the amount of light produced to the amount of the analyte. The relationship between light intensity and amount of analyte can be easily discerned by constructing a calibration curve with known amounts of the analyte. The chemiluminescent compound is typically used in a concentration of about $10^{-5}$ M to about $10^{-2}$ M, preferably between about $10^{-4}$ M and about $10^{-3}$ M. The peroxidase is preferably below about $10^{-9}$ M when detected in a solution. Typical samples which are analyzed by the chemiluminescent reaction method are body fluids such as blood, plasma, serum, urine, semen, saliva, CSF and the like.

Analytes which can be assayed by the present methods include peroxidases, in which case it would be unnecessary to add additional peroxidase, inhibitors of peroxidases, and various classes of organic and biological molecules which can be labeled with a peroxidase or can be specifically detected through enzyme-labeled specific binding partners. The enzyme can be incorporated directly as the label on the analyte binding compound. Alternately the analyte binding compound can be bound to at least one enzyme-labeled specific binding substance for the analyte binding compound. Alternately the analyte binding compound can be labeled with at least one second specific binding substance which is then bound to a enzyme-labeled binding partner for the second specific binding substance.

The present invention also relates to the use of this method for detecting hydrogen peroxide in an assay procedure by a chemiluminescent reaction with a compound of formula I and a peroxidase enzyme, wherein the amount of light produced is related to the amount of the peroxide present. It will be apparent to those skilled in the art of chemiluminescent assays that the present methods can be used to detect oxidase enzymes and dehydrogenase enzymes. These enzymes generate hydrogen peroxide through reduction of oxygen and oxidation of their native substrates. The hydrogen peroxide thereby produced can then be further reacted either concurrently as it is generated or in a subsequent step with compound I of the present invention and a peroxidase to produce light. A property of the light produced is then related to the amount of the oxidase or dehydrogenase enzyme. Further the oxidase or dehydrogenase enzyme may be present as a conjugate to a biological molecule or a member of a specific binding pair in an assay for an analyte.

The reaction of a compound of formula I with a peroxidase to produce chemiluminescence constitutes a rapid and sensitive method for detecting the presence or amount of the peroxidase. Use of the present method can therefore be made for the purpose of determining the presence or quantity of a peroxidase in a sample by measuring the amount or intensity of light produced by reaction of the sample with a compound of formula I. Such a determination can find use e.g. in detecting the peroxidase activity of mammalian blood as evidence in forensic investigations.

A second area of application for the chemiluminescent measurement of peroxidase activity is in the detection and measurement of enzyme inhibitors. Inhibitors can act reversibly by acting as a substrate in competition with a second substrate such as the compounds of the present invention. Another mode of inhibition known as suicide inhibition acts irreversibly by deactivating the enzyme. For example, peroxidase inhibitors include cyanide, sulfide and high concentrations of hydrogen peroxide. Further it is recognized that some substances are only inhibitory at certain concentrations and can be only partially inhibitory.

Measurement of the quantity or characteristics of an inhibitor, such as the inhibition constant $K_i$, or half-life for inhibition, $t_{1/2}$, are made by measuring the enzyme activity of a sample containing the enzyme in question in the presence of a substrate producing a detectable product and a quantity of the inhibitor. In a method of detecting an enzyme inhibitor according to the present invention, a compound of formula I produces light as the detectable product. Reaction of the enzyme and chemiluminescent compound is made in the presence and absence of the inhibitor substance and the results are compared to determine the presence or amount of the inhibitor. The effect of the inhibitor can have one or more of any of three effects, a decrease in light intensity, a slower rate of rise of light intensity or a delay period before light emission begins.

Techniques for performing enzyme assays are well known. With the guidance provided by the examples as taught herein, variations of procedures for preparing samples, determining appropriate quantities and ratios of reagents, reaction times, constructing calibration curves and the like will be within the ability of one of ordinary skill in the art to devise as a matter of routine experimentation.

Since the reaction is catalyzed by the peroxidase, exceedingly small quantities of the enzyme are sufficient to produce a detectable amount of light. Sensitivities below 1 attomol ($1 \times 10^{-18}$ mol) have been achieved. The ability to detect such small amounts of peroxidases make the present chemiluminescent technology suitable for analyses of many types of analytes using enzyme-linked assays. Such analyses and assays require the ability to detect small quantities of peroxidases due to low abundance of the analyte in the sample to be analyzed or to limited sample quantity. In this type of assay, a peroxidase is conjugated to one member of a specific binding pair. An example is a chemiluminescent enzyme-linked immunoassays, such as the so-called enzyme-linked immunosorbent assay or ELISA. Such assays are commonly used in manual format as well as on automated multi-test immunoassay systems. In a typical immunoassay, the analyte hapten, antigen or antibody is assayed by detecting the presence or amount of an enzyme-labeled specific binding partner for the analyte or an enzyme-labeled analog of the analyte. Various assay formats and the protocols for performing the immunochemical steps are well known in the art. These assays fall broadly into two categories. Competitive assays feature an immunological binding of a specific antibody with the analyte and an analyte analog, e.g. a detectably labeled analyte molecule. Sandwich assays result by the sequential or simultaneous binding of two antibodies, one of which is detectably labeled, with the analyte. The detectably labeled binding pair so formed can be assayed with the compounds and methods of the present invention. When the detectable label is the peroxidase enzyme, it is detected directly. When the detectable label is a member of another specific binding pair, e.g. a hapten, a conjugate of its binding partner with a peroxidase is reacted first and the peroxidase then detected in accordance with the present methods. Measurement can be performed with enzyme-labeled species attached to a solid surface or support including beads, tubes, microwells, magnetic particles, test strips, membranes and filters such as are in common use in the art. The detectable enzyme-labeled species can also be present free in solution or enclosed within an organized assembly such as a liposome in which case a lytic agent is employed to lyse the liposome and free the detectable enzyme.

Another exemplary use is the detection of proteins by the technique of Western-blotting. A sample containing a protein of interest as the analyte is subject to electrophoretic separation. The separated proteins are transferred to a blotting membrane such as a nitrocellulose or PVDF membrane by capillary action or with the aid of an electric field. Such transferred protein is typically detected with a specific primary antibody and an enzyme-labeled secondary antibody which recognizes and binds to the primary antibody. Visualization of marker enzyme activity reflects the presence of the analyte protein. To adapt the methods of the present invention for Western blotting, an HRP conjugated secondary antibody can be employed and peroxidase activity measured with chemiluminescence using a compound of the present invention as the chemiluminescent reagent. Variations on this technique such as using biotinylated antibodies and avidin-HRP are considered within the scope of assays able to be performed using the inventive methods.

In addition to the aforementioned antigen-antibody, hapten-antibody or antibody-antibody pairs, specific binding pairs also can include complementary oligonucleotides or polynucleotides, avidin-biotin, streptavidin-biotin, hormone-receptor, lectin-carbohydrate, IgG-protein A, nucleic acid-nucleic acid binding protein and nucleic acid-anti-nucleic acid antibody.

A particularly useful application of the present detection methods is the detection of nucleic acids by the use of enzyme-labeled nucleic acid probes. Methods for analysis and chemiluminescent detection of nucleic acids using enzyme-labels, for example, solution hybridization assays, DNA detection in Southern blotting, RNA by Northern blotting, DNA sequencing, DNA fingerprinting, colony hybridizations and plaque lifts are all well established techniques. The enzyme label (e.g. HRP) can be present as a direct conjugate with a probe oligonucleotide or capture oligonucleotide or it can be incorporated through indirect linking means using art-known methods. Examples of indirect linking means include using hapten-labeled oligonucleotides and anti-hapten-HRP conjugates or biotinylated oligonucleotides and avidin-HRP conjugates. Such nucleic acid assays can be performed on a blotting membrane or in solution using oligonucleotides attached to solid surfaces including beads, tubes, microwells, magnetic particles or test strips such as are known in the art.

In another aspect, the present invention relates to a reagent composition for producing chemiluminescence by reaction with a peroxidase comprising an aqueous buffer with a pH between about 7 and about 10.5, a compound of formula I at a concentration of 0.01–10 mM and a peroxide at a concentration of 0.01–10 mM. Optionally the compositions may further comprise at least one enhancer in an amount effective to enhance the chemiluminescence, preferably between 0.001 and 10 mg/mL and a non-ionic surfactant at a concentration of 0.01 and 10 mg/mL.

A preferred reagent composition for producing chemiluminescence by reaction with a peroxidase comprises an aqueous buffer with a pH between about 7.5 and about 9, an acridan phosphate of formula V or VI at a concentration of 0.01–10 mM, a peroxide at a concentration of 0.01–10 mM, an enhancer at a concentration of 0.001 and 10 mg/mL and a non-ionic surfactant in an amount effective to enhance the chemiluminescence, preferably between 0.001 and 10 mg/mL. The formulation can further comprise a chelating agent such as EDTA at a concentration of 0.01–10 mM.

In order to more fully describe various aspects of the present invention, the following examples are presented which do not limit the scope of the invention in any way.

EXAMPLES

1. Synthesis of Acridan Phosphates

The following compounds were prepared as described in applicant's PCT Application WO 97/26245.

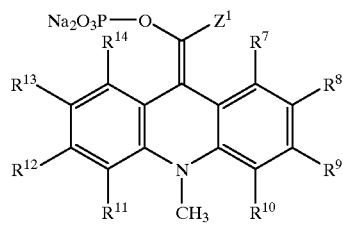

| Compound | $R^7$–$R^{14}$ | $Z^1$ | $R^1$ |
|---|---|---|---|
| 1 | all H | O | phenyl |
| 2 | all H | O | 3,5-difluorophenyl |
| 3 | $R_9$ = $OCH_3$ | O | phenyl |
| 4 | $R_9$ = Cl | O | 2,6-dimethylphenyl |
| 5 | all H | S | phenyl |
| 6 | $R_{11}$—$R_{12}$ = | O | phenyl |

-continued

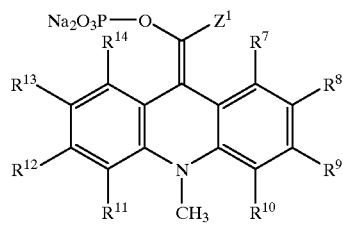

| Compound | $R^7$–$R^{14}$ | $Z^1$ | $R^1$ |
|---|---|---|---|
| 7 | all H | S | 4-fluorophenyl |
| 8 | all H | S | 4-methoxyphenyl |
| 9 | all H | S | 2,6-dimethylphenyl |
| 10 | $R^8$, $R^{13}$ = F | S | phenyl |
| 11 | all H | S | trifluoroethyl |
| 12 | all H | S | 4-chlorophenyl |
| 13 | all H | S | 2-naphthyl |

$R^7$–$R^{14}$ are H unless otherwise indicated. Compounds 3, 4 and 6 were obtained as mixtures of double bond isomers. Each of these compounds functions in the reactions of the present invention to generate chemiluminescence.

2. Acridan Bis(cyanoethyl)phosphate Compounds

Each of compounds 1–13 was prepared by deprotection of the corresponding bis(cyanoethyl)-protected phosphate triester compound 1a–13a having the formula:

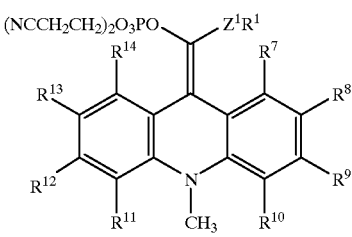

The bis(cyanoethyl) phosphate derivatives also reacted with a peroxide and a peroxidase to produce chemiluminescence.

3. Synthesis of Additional Acridan Phosphate Salt and Acridan Bis(cyanoethyl)phosphate Compounds Additional acridan phosphate salts 14–23 and bis (cyanoethyl) esters 14a–23a which were prepared as described in applicant's PCT Application WO 97/26245 have the formulas

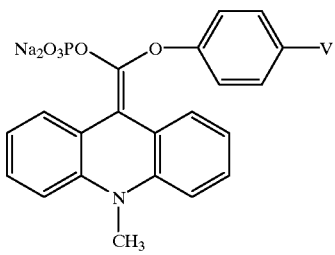

| Compound | V |
|---|---|
| 14 | —C(CH$_3$)$_3$ |
| 15 | CH$_3$ |
| 16 | OCH$_3$ |
| 17 | F |
| 18 | Cl |
| 19 | Br |
| 20 | I |
| 21 | COCH$_3$ |
| 22 | CN |
| 23 | NO$_2$ | as well as the compound 24 (Y=Na) and 24a (Y=CH$_2$CH$_2$CN) having the formula:

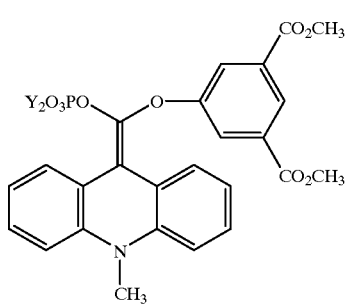

24 and compounds 25–36 (Y=Na) and 25a–36a (Y=CH$_2$CH$_2$CN) having the formula:

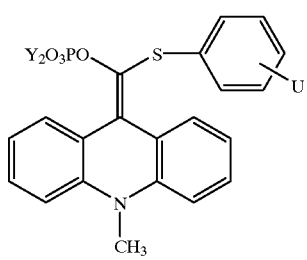

wherein U is p-I (25), p-CH$_3$ (26), m-OCH$_3$ (27), o-Cl (28), m-Cl (29), o-Br (30), m-Br (31), p-Br (32) and p-NO$_2$ (33) as well as compounds of this formula having a 3,4-dichloro- (34), 2,5-dichloro-(35) and 2,6-dichlorophenyl (36) group.

All produce chemiluminescence when reacted with a peroxidase and a peroxide.

The following exemplary compounds were prepared and found to produce chemiluminescence according to the present methods.

7. Synthesis of Acridan Derivative 37

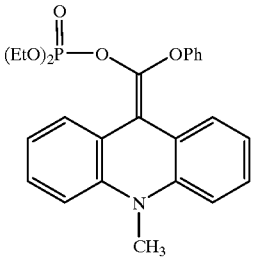

37

A solution of phenyl 10-methylacridan-9-carboxylate (250 mg, 0.79 mmol) in THF was deprotonated with LDA at −78° C. Simultaneously, (EtO)$_2$POCl (205 mg, 1.2 mmol) and pyridine (94 mg, 1.2 mmol) were added via syringes and stirring continued for 15 min. The dry ice bath was removed and stirring continued for 2 h. The volatiles were removed and the product isolated from the residue chromatographically in two steps. A column chromatographic purification using 30% ethyl acetate/hexane allowed separation of the product containing a fluorescent impurity. Final purification was effected by prep. TLC using 10% ethyl acetate/CH$_2$Cl$_2$; $^1$H NMR (acetone-d$_6$) δ1.08 (t, 6H), 3.46 (s, 3H), 3.76–3.97 (m, 4H), 6.79–7.91 (m, 13H).

8. Synthesis of Acridan Derivative 38

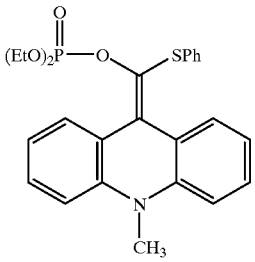

38

A solution of phenyl 10-methylacridan-9-thiocarboxylate (1.0 g, 3 mmol) in THF was deprotonated with LDA at −78° C. Simultaneously, (EtO)$_2$POCl (958 mg, 5 mmol) and pyridine (2.5 mL, 3 mmol) were added via syringes and stirring continued for 15 min. The dry ice bath was removed and stirring continued for 2 h. The volatiles were removed and the product isolated from the residue chromatographically in two steps. A column chromatographic purification using 30–100% ethyl acetate/hexane allowed separation of the product containing blue and green fluorescent impurities. Final purification was effected by prep. TLC using 12% ethyl acetate/CH$_2$Cl$_2$; $^1$H NMR (acetone-d$_6$) δ1.01 (t, 6H), 3.49 (s, 3H), 3.74–3.96 (m, 4H), 6.91–7.45 (m, 11H), 7.78 (d, 1H), 7.99 (d, 1H).

9. Synthesis of Acridan Derivative 39

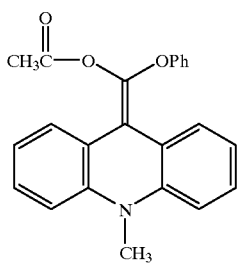

A solution of phenyl 10-methylacridan-9-carboxylate (311 mg, 1 mmol) in THF was added dropwise to a solution of LDA at −78° C. After 30 minutes at −78° C., acetic anhydride (161.3 mg, 1.6 mmol) was added via syringe and the dry ice bath was removed. After one hour, the volatiles were removed and the product isolated from the residue chromatographically. A column chromatographic purification using 5% ethyl acetate/hexane provided a 90 mg pure fraction as a white solid and a second fraction (250 mg) which contained some starting material; $^1$H NMR (CDCl$_3$) δ2.04 (s, 3H), 3.44 (s, 3H), 6.82–7.65 (m, 13H).

10. Synthesis of Acridan Derivative 40

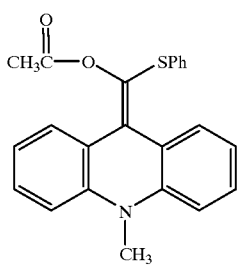

A solution of phenyl 10-methylacridan-9-thiocarboxylate (1.05 g) in THF was deprotonated with LDA at −78° C. Acetic anhydride (0.45 mL) in 10 mL of THF was added dropwise, the dry ice bath was removed and continued stirring over night. The volatiles were removed and the product isolated from the residue chromatographically. A column chromatographic purification using 5–20% ethyl acetate/hexane provided 1.15 g of compound 40 as an off-white solid; $^1$H NMR (CDCl$_3$) δ1.89 (s. 3H), 3.48 (S, 3H), 6.95–7.06 (m, 4H), 7.20–7.34 (m, 5H), 7.40–7.44 (m, 2H), 7.62 (d, 1H), 7.79 (d, 1H).

11. Synthesis of Acridan Derivative 41

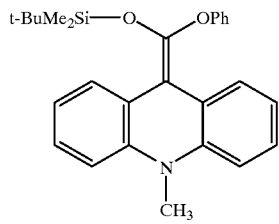

A solution of phenyl 10-methylacridan-9-carboxylate (333.4 mg, 1.06 mmol) in THF was deprotonated with LDA at −78° C. for 30 min. The deep orange solution was treated with t-butyldimethylsilyl chloride (253.4 mg, 1.68 mmol) in 10 mL of dry THF. The dry ice bath was removed and stirring continued for 2 h. The volatiles were removed and the product isolated as an oil (212 mg) from the residue chromatographically using 5% ethyl acetate/hexane; $^1$H NMR (CDCl$_3$) δ−0.12 (s, 6H), 0.77 (s, 9H), 3.37 (s, 3H), 6.75–7.38 (m, 12H), 7.79 (dd, 1H).

12. Synthesis of Acridan Derivative 42

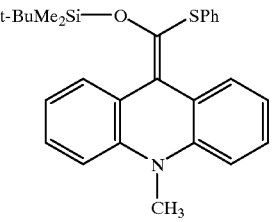

A solution of phenyl 10-methylacridan-9-thiocarboxylate (322.3 mg, 0.97 mmol) in THF was deprotonated with LDA at −78° C. t-Butyldimethylsilyl chloride (270 mg, 1.8 mmol) in 5 mL of dry THF was added rapidly, the dry ice bath was removed and stirring continued for 90 min. The volatiles were removed and 330 mg of the product isolated from the residue chromatographically using 5% ethyl acetate/hexane as an oil which solidified on standing; $^1$H NMR (CDCl$_3$) δ−0.09 (s, 6H), 0.73 (s, 9H), 3.43 (s, 3H), 6.84–7.01 (m, 4H), 7.16–7.47 (m, 7H), 7.73–7.76 (m, 1H), 7.90–7.93 (m, 1H).

13. Synthesis of Compound 43

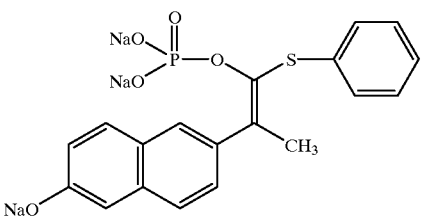

The E isomer is depicted here for illustration. Although substantially one isomer was formed, it is not know with certainty which isomer.

(a) A mixture of 2-(6-hydroxy-2-naphthyl)-propanoic acid (1.00 g) and benzenethiol (0.635 g) in 100 mL of dry THF was treated with 1.2 g of DCC by stirring over night. The mixture was evaporated to dryness and the residue washed with hexane and filtered. The residue was partitioned between CH$_2$Cl$_2$ and water and the organic layer dried and evaporated. The crude thioester phenyl 2-(6-hydroxy-2-naphthyl)-propane-thioate was purified by column chromatography with 30% ethyl acetate/hexane; $^1$H NMR (CDCl$_3$) δ1.66 (d, 3H), 4.14 (q, 1H), 5.30 (s, 1H), 7.09–7.74 (m, 11H); $^{13}$C NMR (CDCl$_3$) δ18.63, 54.09, 103.02, 109.42, 118.35, 126.54, 126.97, 127.06, 127.88, 128.88, 129.18, 129.39, 129.82, 134.04, 134.52, 153.86, 199.78.

(b) The phenol group was protected as the pivalate ester by reacting the product of the previous step (2.5 g) with 1.1 mL of pivaloyl chloride in 3 mL of triethylamine. On completion of the reaction, the mixture was evaporated to dryness and the residue partitioned between CH$_2$Cl$_2$ and water. The organic layer was washed with water followed by satd. NaCl, dried and evaporated. The crude thioester phenyl 2-(6-pivaloyloxy-2-naphthyl)-propanethioate was purified by column chromatography with 0–5% ethyl acetate/hexane; $^1$H NMR (CDCl$_3$) δ1.41 (s, 9H), 1.66 (d, 3H), 4.17 (q, 1H), 7.19–7.87 (m, 11H).

(c) Conversion of the thioester from step (b) to the enol bis(cyanoethyl)phosphate was effected by deprotonation of 2.0 g of the thioester with 1.5 eq. of LDA in dry THF at −78° C. and reacting the enolate with 0.71 mL of POCl$_3$ and 0.62 mL of pyridine, followed by addition of 1.04 mL of 3-hydroxypropionitrile in 1.2 mL of pyridine. The reaction solution was filtered and evaporated. The product was isolated from the residue by column chromatography using 60% ethyl acetate/hexane followed by a further wash with water to remove residual 3-hydroxypropionitrile. The product appeared to be substantially one isomer (43a); $^1$H NMR (CDCl$_3$) δ1.39 (s, 9H), 2.38 (s, 3H), 2.67 (m, 4H), 4.25 (m, 4H), 7.2–7.8 (m, 11H); $^{31}$P NMR (CDCl$_3$) δ−7.43.

(d) Compound 43a was deprotected by reacting 0.72 g in 35 mL of acetone containing 0.198 g of NaOH dissolved in 1 mL of water. The precipitated salt was washed with acetone, dissolved in ethanol and precipitated with acetone to produce 43; $^1$H NMR (CD$_3$OD) δ2.34 (s, 3H), 6.80–7.44 (m, 11H); $^{13}$C NMR (CD$_3$OD) δ21.26, 111.32, 124.15, 125.10, 125.08, 127.38, 127.90, 128.62, 129.35, 129.44, 135.79, 136.06, 136.14, 136.51, 139.31, 139.43, 140.07, 164.99; $^{31}$P NMR (CD$_3$OD) δ6.24.

14. Synthesis of Compound 44

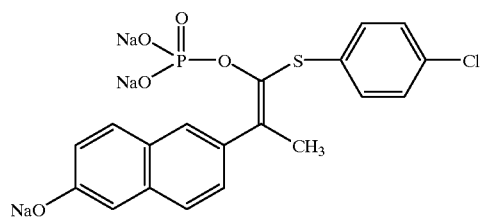

44 E/Z (a) A mixture of 2-(6-hydroxy-2-naphthyl)-propanoic acid (7.00 g) and 4-chlorobenzenethiol (6.22 g) in dry THF was treated with 8.85 g of DCC by stirring over night. The mixture was filtered and the filtrate evaporated to dryness. The residue was partitioned between CH$_2$Cl$_2$ and water and the organic layer washed sequentially with water and satd. NaCl. Drying and evaporating the solvent produced the thioester phenyl 2-(6-hydroxy-2-naphthyl)-propanethioate which was purified by column chromatography with 20% ethyl acetate/hexane; $^1$H NMR (CDCl$_3$) δ1.65 (d, 3H), 4.08–4.18 (m, 1H), 7.11–7.75 (m, 10H).

(b) The phenol group was protected as the pivalate ester. The thioester from the previous step (6.14 g) was reacted with pivaloyl chloride (2.89 g) and 5 mL of triethylamine. After evaporating the mixture to dryness, the residue was washed with water and satd. NaCl and dried over Na$_2$SO$_4$. Further purification was performed by chromatography with 5% ethyl acetate/hexane; $^1$H NMR (CDCl$_3$) δ1.41 (s, 9H), 1.65–1.68 (d, 3H), 4.12–4.19 (q, 1H), 7.20–7.87 (m, 10H); $^{13}$C NMR (CDCl$_3$) δ18.57, 27.22, 39.18, 54.21, 103.02, 118.35, 121.78, 126.57, 126.99, 128.33, 129.39, 131.43, 133.25, 136.74, 149.06, 177.32, 198.59.

(c) Conversion of the protected thioester to the enol bis(cyanoethyl)phosphate was effected by deprotonation of 2.2 g of the thioester with 1.5 eq. of LDA in dry THF at −78° C. and reacting the enolate with 1.5 eq. of POCl$_3$ and 1.5 eq. of pyridine, followed by addition of 1.04 mL of 3-hydroxypropionitrile in 1.2 mL of pyridine. The reaction solution was evaporated, and the residue partitioned between CH$_2$Cl$_2$ and water. The organic layer was washed sequentially with water and satd. NaCl, dried and evaporated. The product was isolated from the residue chromatographically using 65% ethyl acetate/hexane as a mixture of isomers (44a E/Z); $^1$H NMR (CDCl$_3$) δ1.40 (s, 9H), 2.36 & 2.36 (2s, 3H), 2.72–2.76 (m, 4H), 4.24–4.35 (m, 4H), 7.17–7.81 (m, 10H); $^{31}$P NMR (CDCl$_3$) δ−7.07.

(d) Compound 44a was deprotected by reacting 0.80 g in 60 mL of acetone containing 0.26 g of NaOH dissolved in 1 mL of water. The precipitated salt was washed with acetone and dried producing compound 44 as a mixture of isomers (44 E/Z); $^1$H NMR (D$_2$O) δ2.19 (s, 3H), 6.79–7.54 (m, 11H); $^{31}$P NMR (D$_2$O) δ2.90.

15. Synthesis of Compound 45

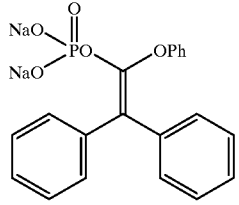

45

(a) Diphenylacetic acid (3.12 g) was converted to the acid chloride by refluxing in 50 mL of SOCl$_2$ for 2.5 hours and esterified with 1.52 g of phenol in 50 mL of CH$_2$Cl$_2$ containing ca. 2 mL of Et$_3$N over night. The volatiles were removed in vacuo and the residue partitioned between hexane and water. The organic layer was dried and the ester used without further purification; $^1$H NMR (CDCl$_3$) δ5.27 (s, 1H), 7.05–7.44 (m, 15H); $^{13}$C NMR (CDCl$_3$) δ57.09, 121.44, 125.99, 127.54, 128.70, 128.82, 129.42, 138.26, 150.79, 171.04.

(b) The ester was converted to the enol bis (cyanoethyl) phosphate by deprotonation of 3.0 g with 1.1 eq. of LDA in dry THF at −78° C. for 30 min. and reacting the enolate with 1.15 eq. of POCl$_3$ and 1.15 eq. of pyridine for 3 hours as the reaction warmed to room temperature. 3-Hydroxypropionitrile (2.05 mL) in 4.8 mL of pyridine was added and the reaction stirred over night. The reaction solution was evaporated, and the residue partitioned between CH$_2$Cl$_2$ and water. The organic layer was washed sequentially with water and satd. NaCl, dried and evaporated. The product was isolated from the residue chromatographically using 70% ethyl acetate/hexane (45a); $^1$H NMR (CDCl$_3$) δ2.30–2.45 (m, 4H), 3.69–3.84 (m, 4H), 7.08–7.45 (m, 15H).

(c) Compound 45a was deprotected by reacting 1.04 g in 30 mL of acetone containing 0.18 g of NaOH dissolved in 1 mL of water over night. The precipitated salt was washed with acetone and dried producing compound 45 (0.5 g); $^1$H NMR (D$_2$O) δ7.00–7.56 (m, 15H); $^{13}$C NMR (D$_2$O) δ110.51, 110.60, 116.21, 122.29, 126.60, 126.72, 128.26, 129.54, 129.87, 129.96, 139.01, 146.75, 146.87, 156.55, 201.63; $^{31}$P NMR (D$_2$O) δ2.15.

15. Synthesis of Compound 46

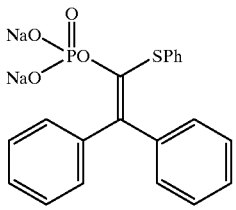

46

(a) Diphenylacetic acid (6.0 g) was converted to the acid chloride by refluxing in 30 mL of SOCl$_2$ and esterified with 3.5 g of thiophenol in 50 mL of CH$_2$Cl$_2$ containing ca. 10 mL of Et$_3$N over night. The solution was extracted sequentially with water, saturated NaHCO$_3$ and brine. After drying over Na$_2$SO$_4$, the volatiles were removed in vacuo and the thioester used without further purification; $^1$H NMR (CDCl$_3$) δ5.31 (s, 1H), 7.2–7.6 (m, 15H);

(b) The thioester was converted to the enol bis (cyanoethyl)phosphate by deprotonation of 3.0 g with 1.1 eq. of LDA in dry THF at –78° C. for 30 min. and reacting the enolate with 1.15 eq. of POCl$_3$ and 1.15 eq. of pyridine for 3.5 hours as the reaction warmed to room temperature. 3-Hydroxy-propionitrile (2.05 mL) in 4.8 mL of pyridine was added and the reaction stirred over night. The reaction solution was evaporated, and the residue partitioned between CH$_2$Cl$_2$ and water. The organic layer was washed sequentially with water and satd. NaCl, dried and evaporated. The product was isolated from the residue chromatographically using 65% ethyl acetate/hexane (46a); $^1$H NMR (CDCl$_3$) δ2.3–2.5 (m, 4H), 3.62–3.82 (m, 4H), 7.2–7.45 (m, 15H).

(c) Compound 46a was deprotected by reacting 1.79 g in 50 mL of acetone containing 0.3 g of NaOH dissolved in 2-mL of water over night. The precipitated salt was washed with acetone and dried producing compound 46 (1.5 g); $^1$H NMR (D$_2$O) δ7.08–7.44 (m, 15H); $^{13}$C NMR (D$_2$O) δ125.78, 127.23, 127.41, 127.60, 128.11, 128.17, 129.11, 129.93, 129.54, 135.58, 135.67, 139.86, 140.74, 140.86, 141.62; $^{31}$P NMR (D$_2$O) δ2.30.

16. Synthesis of Compound 47

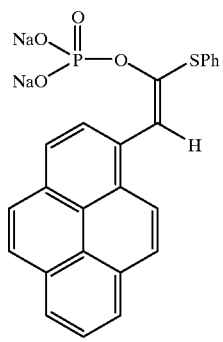

47 E/Z (a) A mixture of 1-pyreneacetic acid (3.00 g) and benzenethiol (1.27 g) in 100 mL of dry THF was treated with 2.38 g of DCC by stirring over night. The mixture was filtered and the filtrate evaporated to dryness. The residue was partitioned between CH$_2$Cl$_2$ and water and the organic layer washed sequentially with satd. NaHCO$_3$, water and satd. NaCl. Drying and evaporating the solvent produced the thioester phenyl 2-pyrenethioacetate which was purified by chromatography using 15% ethyl acetate/hexane; $^1$H NMR (CDCl$_3$) δ4.66 (s, 2H), 7.35 (s, 5H), 8.02–8.30 (m, 9H); $^{13}$C NMR (CDCl$_3$) δ109.23, 124.96, 125.51, 127.45, 127.66, 128.33, 129.15, 129.39, 134.49, 170.01.

(b) Conversion of the thioester to the enol bis (cyanoethyl)phosphate was effected by deprotonation of 0.5 g of the thioester with 1.2 eq. of LDA in 30 mL of dry THF at –78° C. and reacting the enolate with 1.2 eq. of POCl$_3$ and 1.2 eq. of pyridine, followed by addition of 0.255 mL of 3-hydroxypropionitrile in 0.30 mL of pyridine. The reaction solution was evaporated, and the residue partitioned between CH$_2$Cl$_2$ and water. The organic layer was washed sequentially with water and satd. NaCl, dried and evaporated. The product was isolated from the residue chromatographically using 60% ethyl acetate/hexane as a 5:2 mixture of isomers (47a E/Z); $^1$H NMR (CDCl$_3$) δ2.15–2.24 (m), 2.24 (m), 2.63–2.67 (m) 3.62–3.78 (m), 4.14–4.22 (m), 7.24–8.26 (m); $^{31}$P NMR (CDCl$_3$) δ27.39, 28.16; $^{13}$C NMR (CDCl$_3$) δ19.06, 19.15, 19.54, 19.64, 62.40, 62.46, 62.98, 63.04, 116.16, 116.49, 123.51, 123.75, 124.39, 124.54, 124.71, 124.81, 125.57, 125.63, 125.72, 125.87, 126.18, 126.39, 127.09, 127.15, 127.32, 127.46, 127.88, 128.06, 128.17, 128.27, 128.30, 128.76, 129.33, 129.42, 129.76, 129.82, 130.67, 130.85, 131.03, 131.22, 131.31, 131.40, 132.91, 141.32, 142.96, 143.11.

(c) Compound 47a was deprotected by reacting 0.247 g in 6 mL of acetone containing 0.04 g of NaOH dissolved in 0.1 mL of water. The precipitated salt was washed with acetone and dried producing compound 47 as a mixture of isomers (47 E/Z); $^1$H NMR (D$_2$O) δ6.22 (s), 6.74–8.1 (m), 8.47 (d); $^{31}$P NMR (D$_2$O) δ0.12, 0.69, 0.70.

17. Synthesis of Compound 48

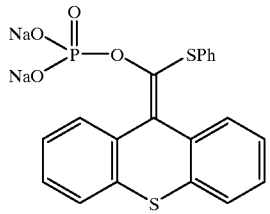

48

(a) A solution of thioxanthone (10 g) in 60 mL of benzene was treated with 5.0 g of LAH by stirring for 15 min. The mixture was heated and 100 mL of ether was added carefully. Reflux was continued for 90 min. The cooled mixture was neutralized with water. The solids were filtered off and the filtrate evaporated to dryness. Pure thioxanthene (9.1 g, 98%) was isolated by chromatography using 20% ethyl acetate/hexane; $^1$H NMR (CDCl$_3$) δ3.82 (s, 3H), 7.21 (m, 4H), 7.33 (m, 2H), 7.46 (m, 2H).

(b) Thioxanthene, 9.1 g, was dissolved in 100 mL of dry THF. The solution was cooled in an ice bath and n-BuLi (24 mL of 2.5 M solution) was added dropwise. The red solution was stirred at room temperature for one hour. Powdered CO$_2$ was added (ca. 150 g) causing formation of a white precipitate. After stirring an additional hour the mixture was evaporated and the residue dissolved in water. The aqueous solution was extracted with CH$_2$Cl$_2$, and neutralized with HCl. The precipitated product was dissolved in ether, dried and evaporated producing thioxanthene-9-carboxylic acid as a white solid (8.8 g): $^1$H NMR (DMSO-d$_6$) δ5.25 (s, 1H), 7.30 (m, 4H), 7.49 (m, 4H), 12.60 (s, 1H).

(c) Thioxanthene-9-carboxylic acid (5.8 g) and thionyl chloride (30 mL) were stirred at room temperature for 1 h. The thionyl chloride was evaporated and the residue dissolved in 100 mL of $CH_2Cl_2$. Pyridine (4 mL) and thiophenol (4 g) were added and the reaction mixture stirred at room temperature for 5 h. The mixture was evaporated and the residue washed with water followed by ether. The thioester was purified by chromatography using 20% ethyl acetate/hexane yielding 6.3 g of pure phenyl thioxanthene-9-thiocarboxylate: $^1H$ NMR ($CDCl_3$) δ5.16 (s, 1H), 7.32 (m, 9H), 7.50 (m, 4H); $^{13}C$ NMR ($CDCl_3$) δ63.0, 126.9, 127.3, 128.1, 128.4, 129.2, 129.4, 130.9, 132.4, 133.7, 134.5, 196.5.

(d) The thioester (4.6 g) was deprotonated with 1.5 eq. Of LDA in 40 mL of dry THF at –78° C. for 30 min. A solution of $POCl_3$ (3.2 g) and pyridine (1.66 g) in 10 mL of dry THF was added dropwise to the reaction which was allowed to warm to room temperature. After stirring at room temperature for 45 min, a solution of cyanoethanol (5.68 g) and pyridine (6.3 g) was added and stirring continued over night. The mixture was filtered and the filtrate concentrated to a thick residue which was chromatographed using 70% ethyl acetate/hexane. The enol bis(cyanoethyl)phosphate (48a) was obtained as a foam (3.1 g); $^1H$ NMR ($CDCl_3$) δ2.52 (m, 4H), 3.94 (m, 4H), 7.20–7.48 (m, 10H), 7.55 (dd, 1H), 7.74 (dd, 1H), 7.85 (dd, 1H); $^{13}C$ NMR ($CDCl_3$) δ19.5, 62.5, 116.6, 126.2, 126.3, 126.7, 127.0, 127.1, 128.0, 128.1, 128.2, 129.1, 129.5, 129.7, 132.5, 133.0, 133.3, 134.2, 134.3, 134.6, 137.7, 137.8; $^{31}P$ NMR ($CDCl_3$) δ–10.35 (p).

(e) Compound 48a was deprotected by reacting 1.8 g in 40 mL of argon-purged acetone containing 0.28 g of NaOH dissolved in 5.6 mL of water over night. The precipitated salt was washed with 10% aq. acetone and dried producing compound 48 (1.57 g) as a white solid; $^1H$ NMR ($D_2O$) δ6.94–7.25 (m, 9H), 7.38 (m, 2H), 7.76 (d, 1H), 8.08 (d, 1H); $^{31}P$ NMR ($D_2O$) δ0.73 (s).

18. Synthesis of Compound 49

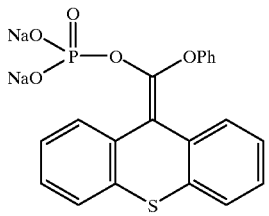

Compound 49 was prepared by the sequence of reactions described in the previous example substituting phenol for thiophenol in step (c).

(a) Phenyl thioxanthene-9-thiocarboxylate: $^1H$ NMR ($CDCl_3$) δ5.26 (s, 1H), 6.94 (d, 2H), 7.15 (t, 1H), 7.24–7.34 (m, 6H), 7.51 (m, 4H).

(b) 9-(Phenoxyphosphoryloxymethylidene)thioxanthene, bis(cyanoethyl)ester (49a); $^1H$ NMR ($CDCl_3$) δ2.50 (m, 4H), 3.84 (m, 2H), 4.02 (m, 2H), 7.16 (m, 5H), 7.29–7.54 (m, 7H), 7.82 (d, 1H); $^{13}C$ NMR ($CDCl_3$) δ19.5, 63.0, 124.1, 126.4, 126.5, 126.8, 127.5, 127.8, 128.0, 129.2, 130.1, 131.2, 131.4, 133.4, 134.4, 142.7, 142.9, 155.0; $^{31}P$ NMR ($CDCl_3$) δ–10.92 (p)

(c) 9-(Phenoxyphosphoryloxymethylidene)thioxanthene, disodium salt (49); $^1H$ NMR ($D_2O$) δ6.92 (t, 1H) 7.04 (t, 2H), 7.07–7.34 (m, 6H), 7.38 (t, 1H), 7.45 (d, 1H), 7.71 (d, 1H), 8.05 (d, 1H); $^{31}P$ NMR ($D_2O$) δ0.22 (s).

19. Synthesis of Compound 50

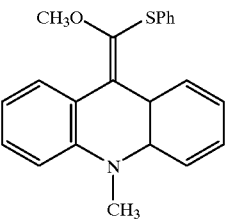

Phenyl 10-methylacridan-9-thiocarboxylate, 1.0 g was converted to the enolate with LDA in 60 mL of dry THF at –70° C. After maintaining the temperature at –70° C. for 1 h, 0.76 g of methyl triflate was added and the reaction mixture was allowed to warm to room temperature. The mixture was allowed to stand for 4 days. $CH_2Cl_2$ (150 mL) was added, the solution was extracted with water and dried on $Na_2SO_4$. The crude product was purified by prep. TLC with a 70/30 hexane:$CH_2Cl_2$ eluent. $^1H$ NMR ($CDCl_3$) δ3.53 (s, 3H), 3.56 (s, 3H), 6.93–7.45 (m, 11H), 7.71 (d, 1H), 7.93 (d, 1H).

20. Chemiluminescent Detection of HRP with Acridan Phosphate 5

Reagent compositions comprising 0.055 M tris buffer, pH 8.6, 0.25 mM urea peroxide, 0.05 mM p-phenylphenol, 0.5 mM EDTA, 0.0125% Tween 20 and $3.3\times10^{-4}$ M acridan 5 were tested for production of chemiluminescence by reacting triplicate 100 μL aliquots with 10 μL of solutions of HRP in water containing between $1.4\times10^{-15}$ and $1.4\times10^{-19}$ moles of enzyme. Light production ensued upon mixing and was measured at 5, 10 and 15 min. The relation between chemiluminescence intensity at 15 min and amount of enzyme is depicted in FIG. 1.

21. Chemiluminescent Detection of HRP with Acridan Phosphate 13

Figure 2:
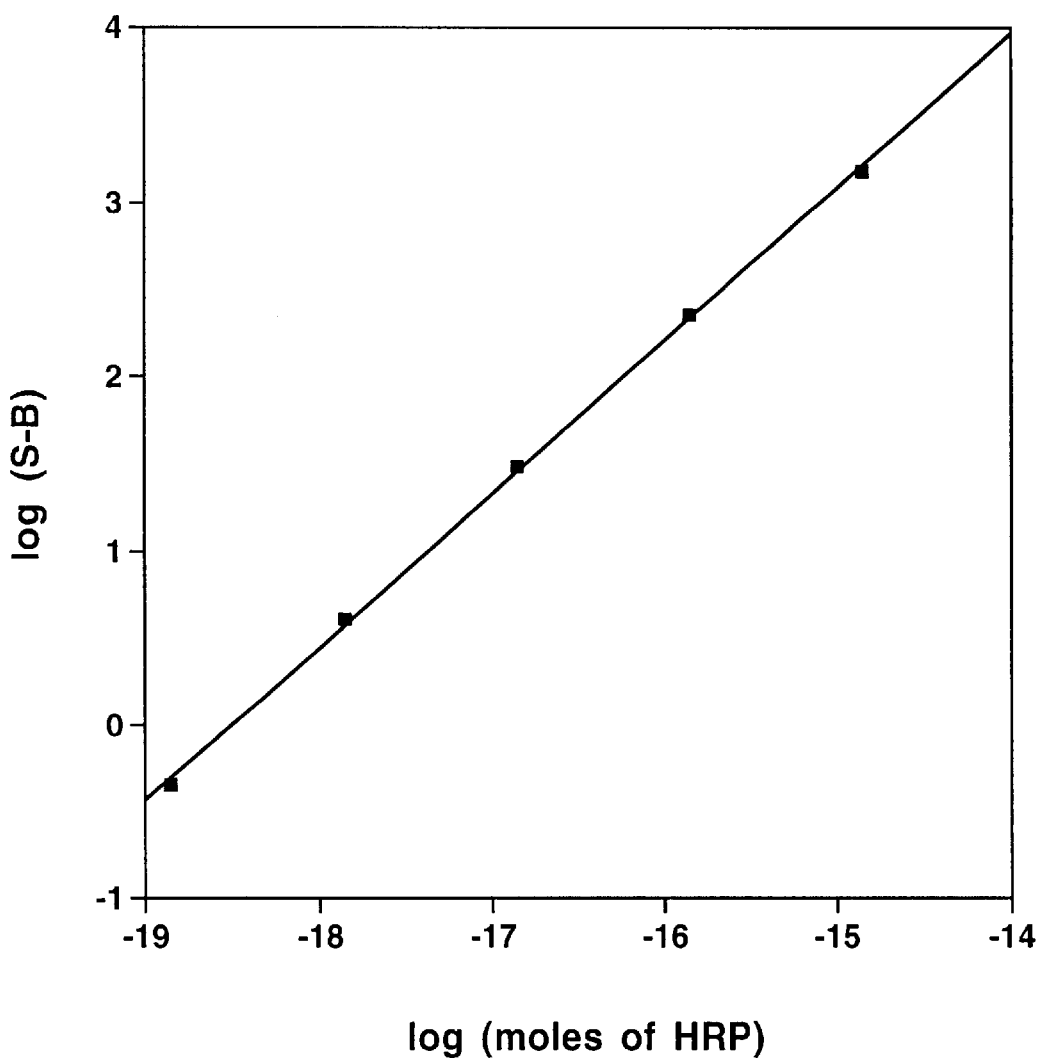
FIG. 2 is a graph relating the amount of HRP to the chemiluminescence intensity at 15 min emitted by 100 μL of a reagent described in Example 21 containing acridan phosphate 13 triggered at room temperature. Chemiluminescence emission was initiated by addition of 10 μL of solutions of HRP containing between $1.4 \times 10^{-15}$ and $1.4 \times 10^{-19}$ moles of enzyme to 100 μL of a reagent comprising 0.055 M tris buffer, pH 8.6, 0.25 mM urea peroxide, 0.05 mM p-phenylphenol, 0.5 mM EDTA, 0.0125% Tween 20 and $3.3 \times 10^{-4}$ M acridan 13 in a black microplate.

Reagent compositions comprising 0.055 M tris buffer, pH 8.6, 0.25 mM urea peroxide, 0.05 mM p-phenylphenol, 0.5 mM EDTA, 0.0125% Tween 20 and $3.3\times10^{-4}$ M acridan 13 were tested for production of chemiluminescence by reacting triplicate 100 μL aliquots with 10 μL of solutions of HRP in water containing between $1.4\times10^{-15}$ and $1.4\times10^{-19}$ moles of enzyme. Light production ensued upon mixing and was measured at 15 min. The relation between chemiluminescence intensity and amount of enzyme is depicted in FIG. 2.

22. Chemiluminescent Detection with Acridan Phosphates 1–4 and 6–12 and 14

In the manner of Example 21, compositions containing each of compounds 1–4 and 6–12 and 14 were reacted with HRP at 25° C. Each produced easily measurable chemiluminescence discernable above the background measured in the absence of HRP.

23. Kinetic Profile of Chemiluminescence Intensity

Figure 3:
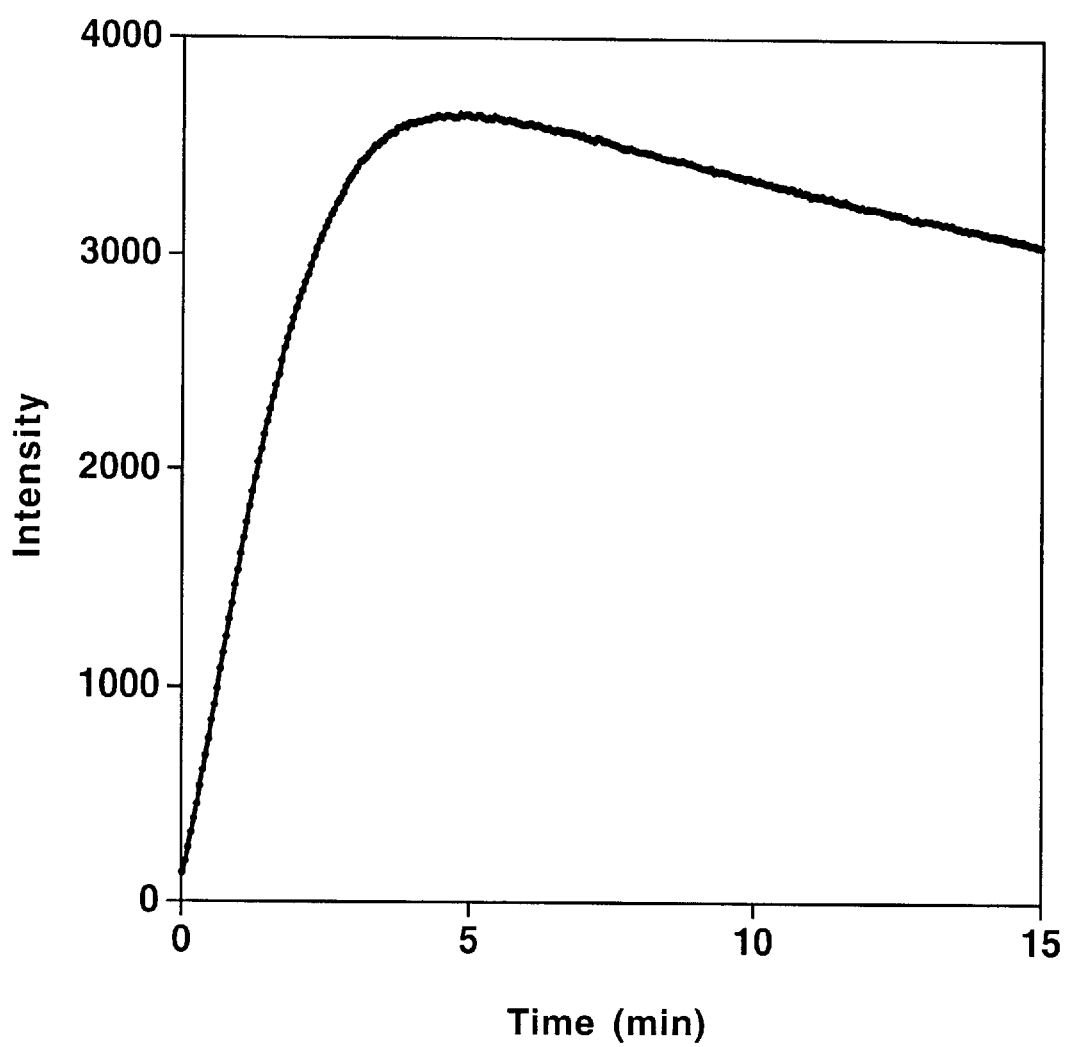
FIG. 3 is a graph showing the time profile of chemiluminescence resulting from reaction of $1.4 \times 10^{-15}$ moles of HRP at 25° C. with 100 μL of the reagent containing acridan 5 described in Example 20.
Figure 4:
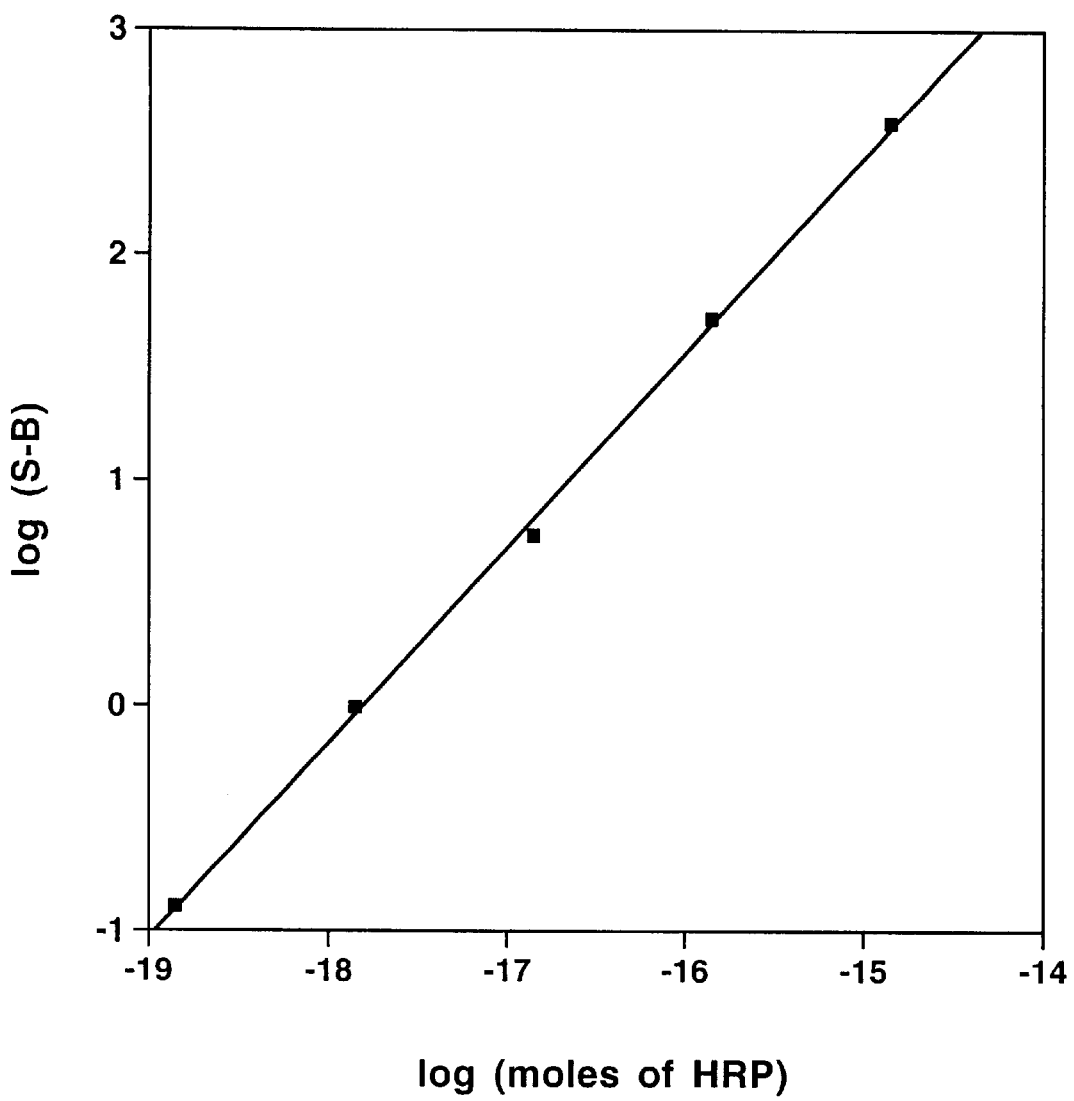
FIG. 4 is a graph relating the amount of HRP to the maximum chemiluminescence intensity at 2 min emitted by 100 μL of a reagent containing acridan 37 triggered at room temperature. Chemiluminescence emission was initiated by addition of 10 μL of solutions of HRP containing between $1.4 \times 10^{-14}$ to $1.4 \times 10^{-19}$ moles to 100 μL of reagent composition comprising 0.01 M tris buffer, pH 8.0, 0.5 mM urea peroxide, 0.1 mM p-phenylphenol, 1 mM EDTA, 0.025% Tween 20 and $5 \times 10^{-5}$ M acridan 37.

The chemiluminescence profile of acridan phosphate 5 reacted with HRP is depicted in FIG. 3. Reaction of 100 μL of the reagent composition of Example 20 with $1.4\times10^{-15}$ mol of HRP at 25° C. caused an instant rise in light emission which achieved maximum intensity in ca. 5 min.

24. Chemiluminescent Detection of HRP with Acridan Diethyl Phosphate 37

Reagent compositions comprising 0.01 M tris buffer, pH 8.0, 0.5 mM urea peroxide, 0.1 mM p-phenylphenol, 1 mM EDTA, 0.025% Tween 20 and $5\times10^{-5}$ M acridan 37 were tested for production of chemiluminescence by reacting triplicate 100 μL aliquots with 10 μL of HRP in the range $1.4\times10^{-14}$ to $1.4\times10^{-19}$ moles. Light production ensued upon mixing and was measured at 2 min. The relation between chemiluminescence intensity and amount of enzyme is depicted in FIG. 4.

25. Chemiluminescent Detection of HRP with Acridan Diethyl Phosphate 38

Figure 5:
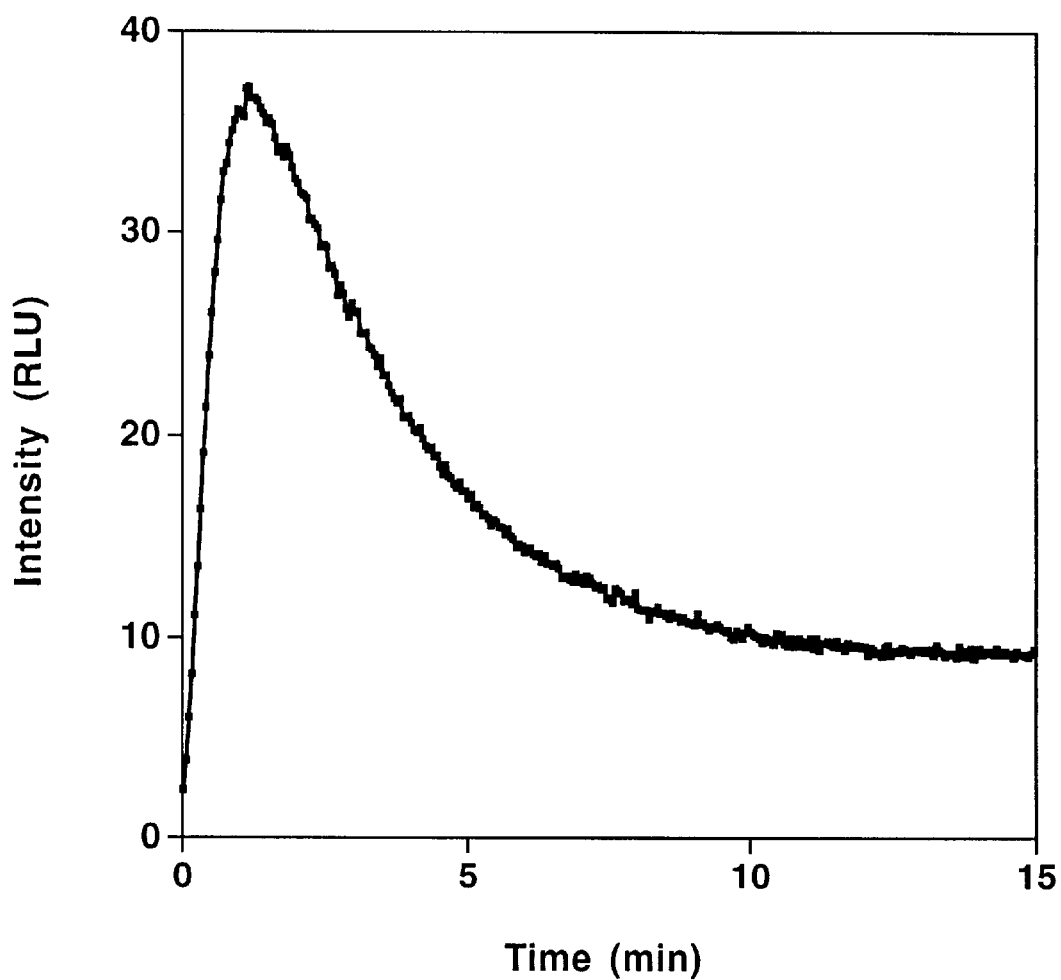
FIG. 5 is a graph showing the time profile of chemiluminescence resulting from reaction of $1.4 \times 10^{-15}$ moles of HRP at 25° C. with 40 μL of a reagent comprising 0.01 M tris buffer, pH 8.0, 0.5 mM urea peroxide, 0.1 mM p-phenylphenol, 1 mM EDTA, 0.025% Tween 20 and $5 \times 10^{-5}$ M acridan 38. Light production ensued upon mixing and reached maximum intensity in 1 min.

A reagent composition (40 µL) comprising 0.01 M tris buffer, pH 8.0, 0.5 mM urea peroxide, 0.1 mM p-phenylphenol, 1 mM EDTA, 0.025% Tween 20 and $5\times10^{-5}$ M acridan 38 was reacted with 1 µL of a solution containing $1.4\times10^{-15}$ moles of HRP. Light production ensued upon mixing and reached maximum intensity in 1 min. The chemiluminescence time profile is depicted in FIG. 5.

26. Chemiluminescent Detection of HRP with Acridan Acetate 39

Figure 6:
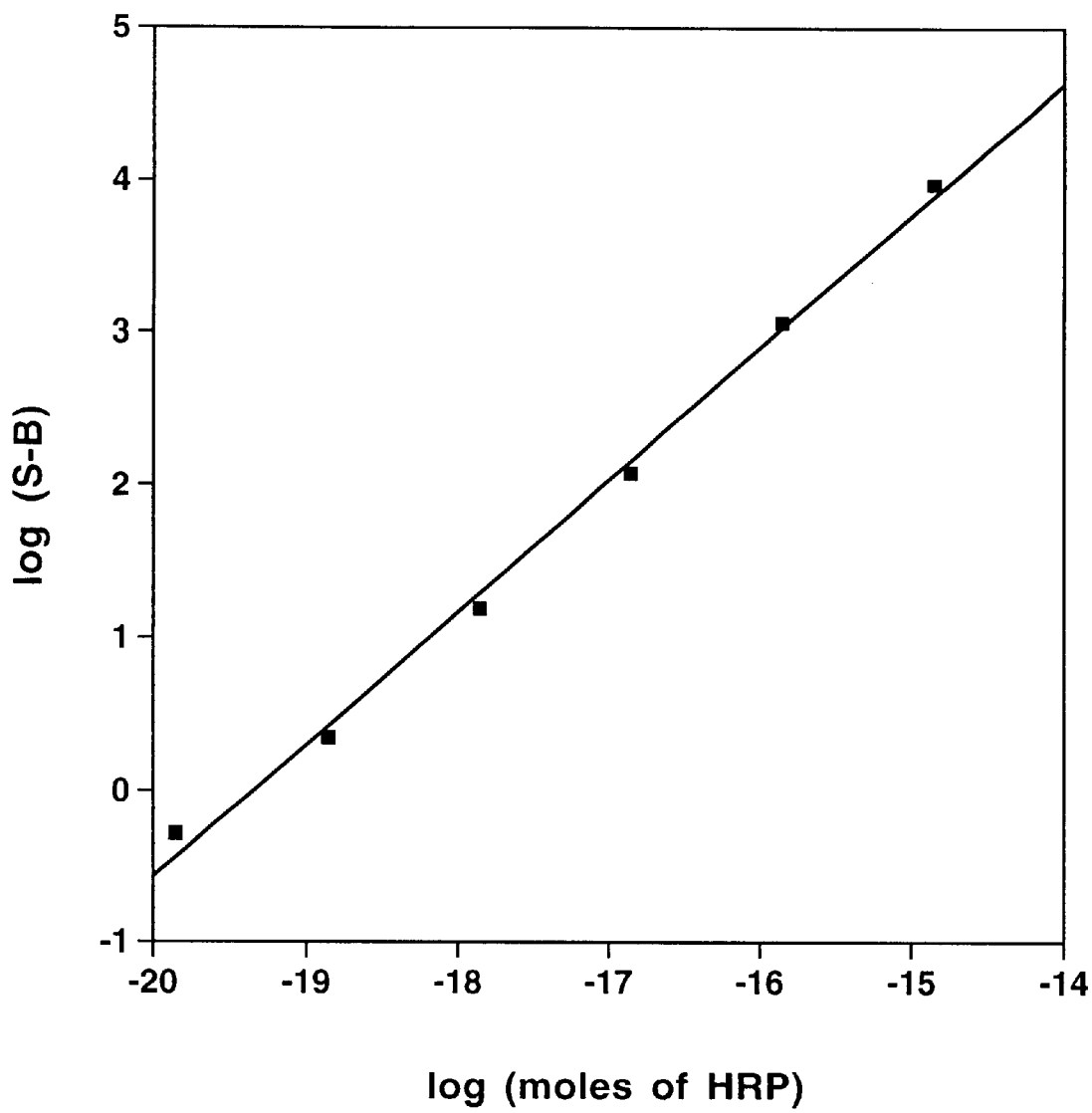
FIG. 6 is a graph relating the amount of HRP to the maximum chemiluminescence intensity at 30 min emitted by 100 μL of a reagent containing acridan 39 triggered at room temperature. Chemiluminescence emission was initiated by addition of 10 μL of solutions of HRP containing between $1.4 \times 10^{-15}$ to $1.4 \times 10^{-20}$ moles to 100 μL of reagent composition comprising 0.01 M tris buffer, pH 8.0, 0.5 mM urea peroxide, 0.1 mM p-phenylphenol, 1 mM EDTA, 0.025% Tween 20 and $5 \times 10^{-5}$ M acridan 39.

Reagent compositions comprising 0.01 M tris buffer, pH 8.0, 0.5 mM urea peroxide, 0.1 mm p-phenylphenol, 1 mM EDTA, 0.025% Tween 20 and $5\times10^{-5}$ M acridan 39 were tested for production of chemiluminescence by reacting triplicate 100 µL aliquots with 10 µL of HRP in the range $1.4\times10^{-15}$ to $1.4\times10^{-20}$ moles. Light production ensued upon mixing and reached maximum intensity in 30 min. The relation between chemiluminescence intensity and amount of enzyme is depicted in FIG. 6.

27. Chemiluminescent Detection of HRP with Acridan Acetate 40

A reagent composition (100 µL) comprising 0.01 M tris buffer, pH 8.0, 0.5 mM urea peroxide, 0.1 mM p-phenylphenol, 1 mM EDTA, 0.025% Tween 20 and $5\times10^{-5}$ M acridan 40 was reacted with 10 µL of a solution containing $1.4\times10^{-15}$ moles of HRP. Light production ensued upon mixing and reached maximum intensity in 7 min.

28. Chemiluminescent Detection of HRP with Acridan 50

Figure 7:
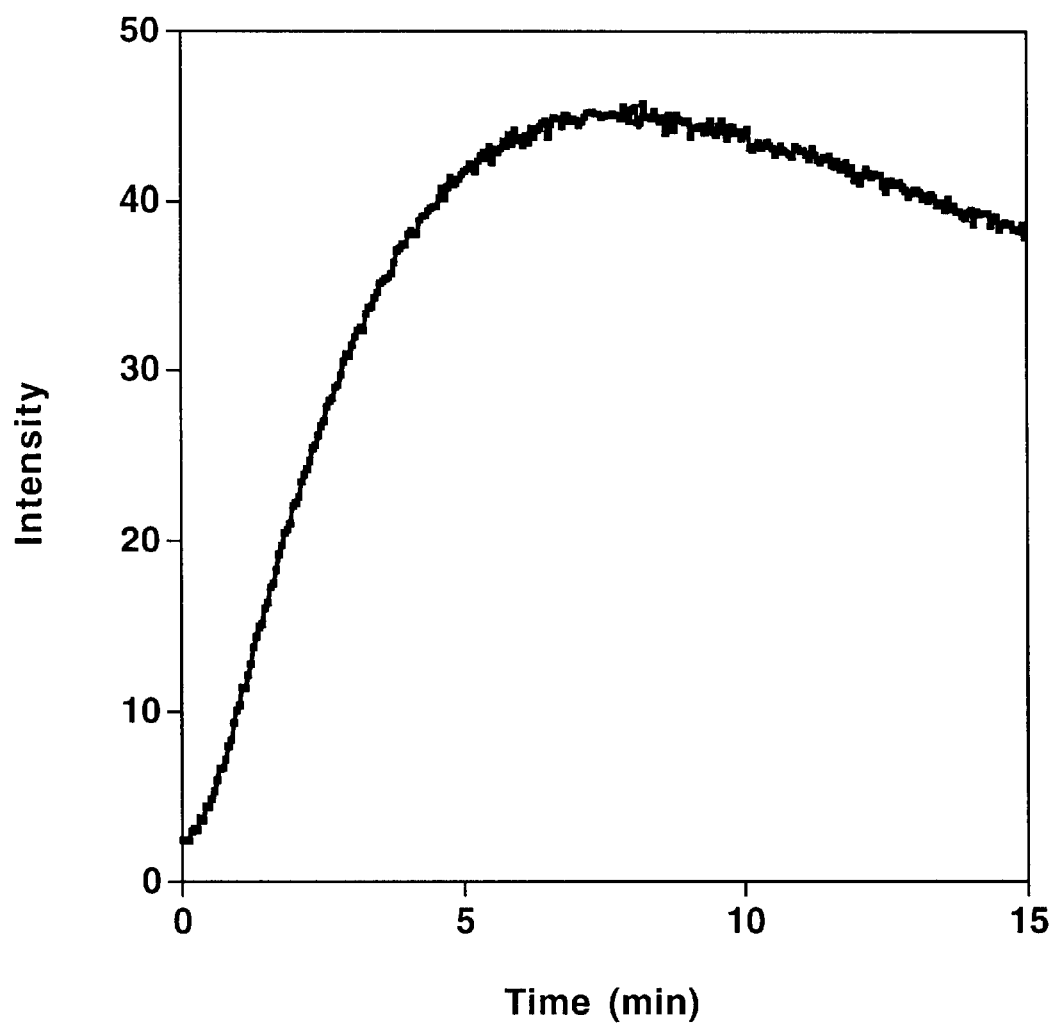
FIG. 7 is a graph showing the time profile of chemiluminescence resulting from reaction of $3.5 \times 10^{-16}$ moles of HRP at 25° C. with 100 μL of a reagent comprising 0.01 M tris buffer, pH 8.0, 0.5 mM urea peroxide, 0.1 mM p-phenylphenol, 1 mM EDTA, 0.025% Tween 20 and $5 \times 10^{-5}$ M acridan 50. Light production ensued upon mixing and reached maximum intensity in 7 min.

A reagent composition (100 µL) comprising 0.01 M tris buffer, pH 8.0, 0.5 mM urea peroxide, 0.1 mM p-phenylphenol, 1 mM EDTA, 0.025% Tween 20 and $5\times10^{-5}$ M acridan 50 was reacted with 2.5 µL of a solution containing $3.5\times10^{-16}$ moles of HRP. Light production ensued upon mixing and reached maximum intensity in 7 min. The chemiluminescence time profile is depicted in FIG. 7.

29. Chemiluminescent Detection of HRP with Compound 43

Figure 8:
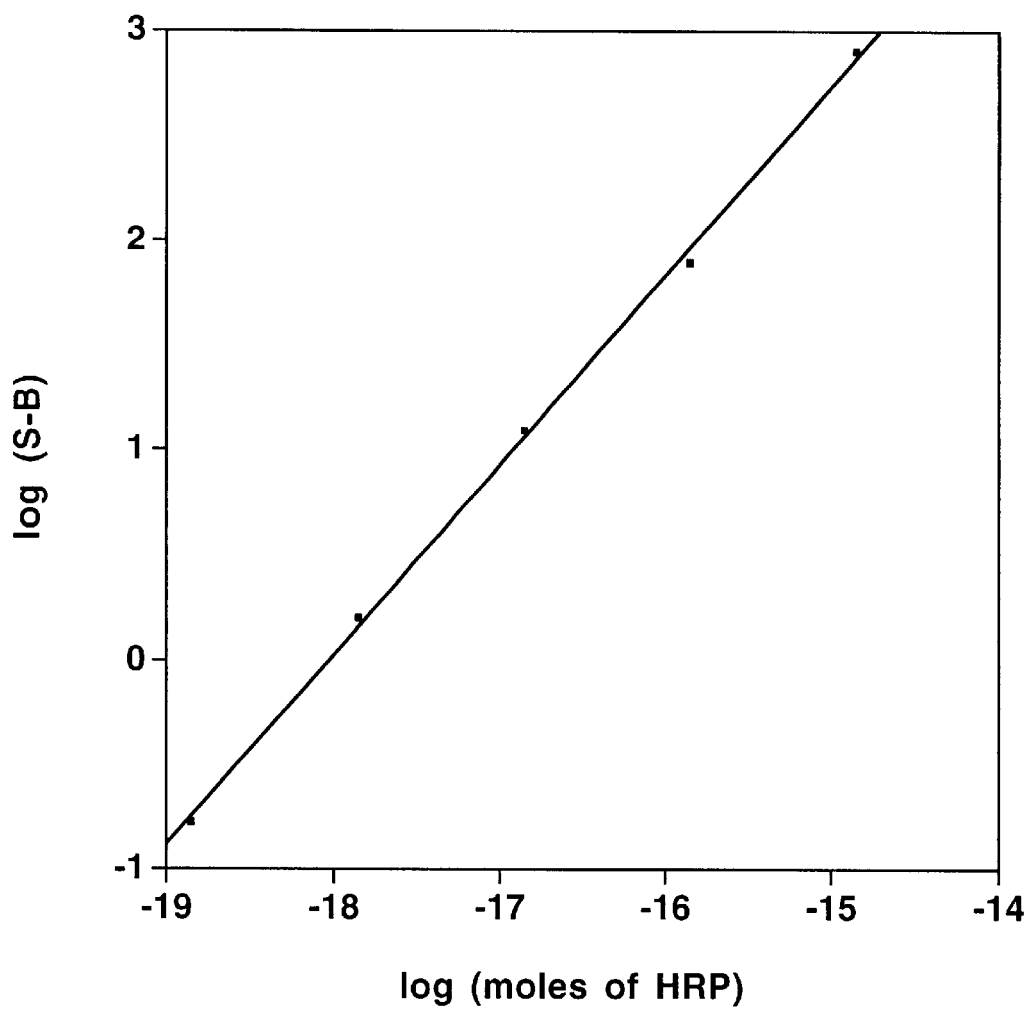
FIG. 8 is a graph relating the amount of HRP to the maximum chemiluminescence intensity at 15 min emitted by 100 μL of a reagent containing acridan 43 triggered at room temperature. Chemiluminescence emission was initiated by addition of 10 μL of solutions of HRP containing between $1.4 \times 10^{-15}$ to $1.4 \times 10^{-19}$ moles to 100 μL of a reagent composition comprising 0.055 M tris buffer, pH 8.6, 0.25 mm urea peroxide, 0.05 mM p-phenylphenol, 0.5 mM EDTA, 0.0125% Tween 20, 1 mM CTAB and $6.6 \times 10^{-4}$ M acridan 43.

Reagent compositions comprising 0.055 M tris buffer, pH 8.6, 0.25 mM urea peroxide, 0.05 mM p-phenylphenol, 0.5 mM EDTA, 0.0125% Tween 20, 1 mM CTAB and $6.6\times10^{-4}$ M acridan 43 were tested for production of chemiluminescence by reacting triplicate 100 µL aliquots with 10 µL of solutions of HRP containing between $1.4\times10^{-15}$ and $1.4\times10^{-19}$ moles of HRP. The relation between chemiluminescence intensity at 15 min and amount of enzyme is depicted in FIG. 8.

Figure 9:
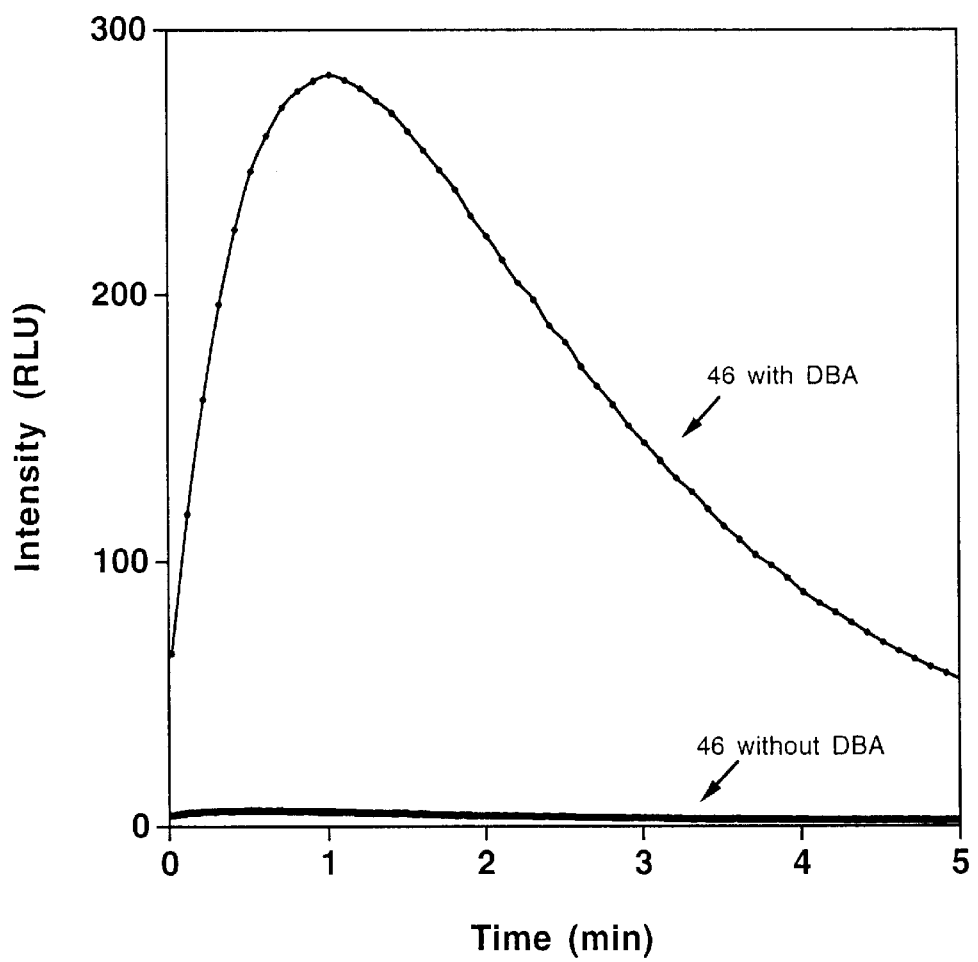
FIG. 9 is a graph demonstrating the enhancement of chemiluminescence by the use of a fluorescent energy transfer agent. Reagent compositions comprising 0.055 M tris buffer, pH 8.6, 0.25 mm urea peroxide, 0.05 mM p-phenylphenol, 0.5 nM EDTA, 0.0125% Tween 20, 1 mM CTAB and $3.3 \times 10^{-4}$ M compound 46 alone or with 50 μM DBA were tested for production of chemiluminescence by reacting a 100 μL aliquot with $3.5 \times 10^{-15}$ moles of HRP.

30. Chemiluminescent Detection of HRP with Compound 46 and Enhancement of Chemiluminescence with Energy Transfer Agent Reagent compositions comprising 0.055 M tris buffer, pH 8.6, 0.25 mM urea peroxide, 0.05 mM p-phenylphenol, 0.5 mM EDTA, 0.0125% Tween 20, 1 mM CTAB and $6.6\times10^{-4}$ M compound 46 alone or with 50 µM DBA were tested for production of chemiluminescence by reacting a 100 µL aliquot with $3.5\times10^{-15}$ moles of HRP. The relative chemiluminescence time profiles are depicted in FIG. 9 and demonstrate the enhancement of chemiluminescence by the triplet energy acceptor DBA.

31. Chemiluminescent Detection of HRP with Compound 48

Figure 10:
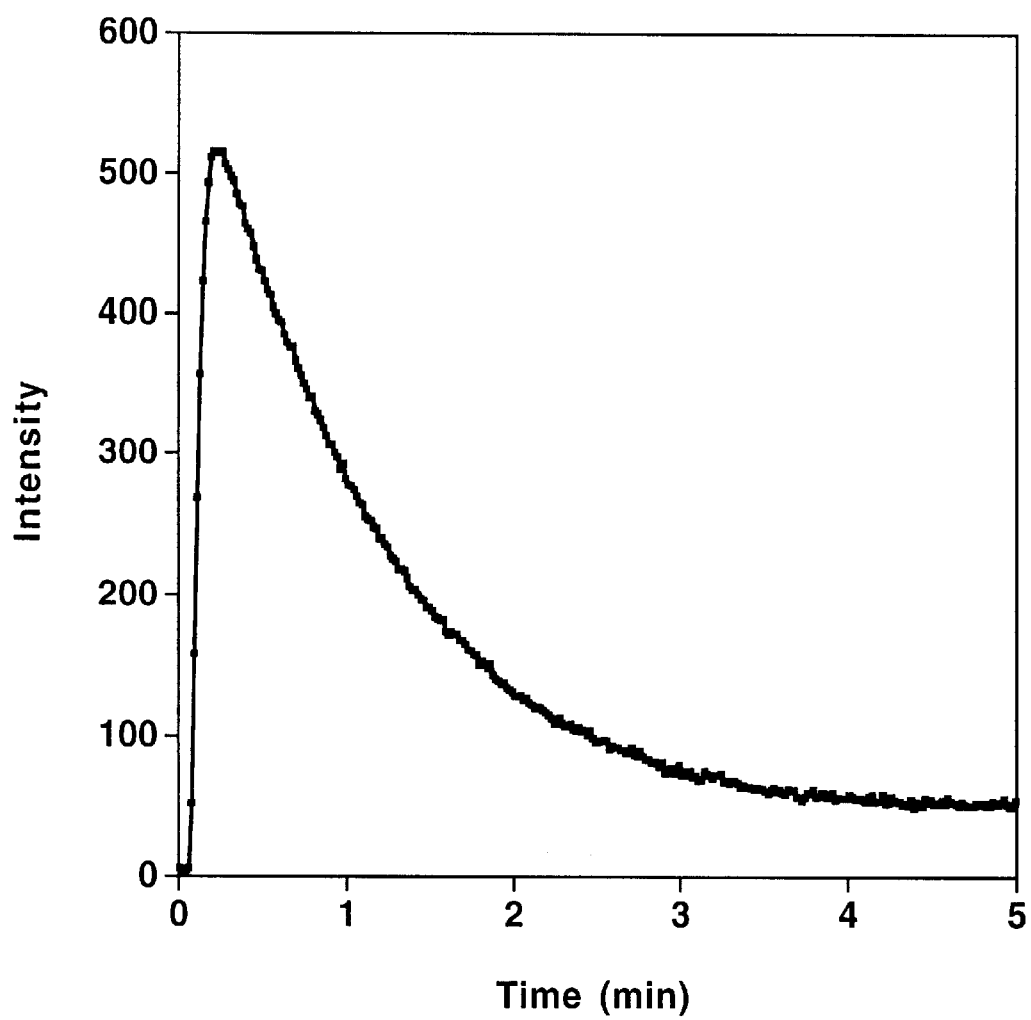
FIG. 10 is a graph showing the time profile of chemiluminescence resulting from reaction of $3.5 \times 10^{-15}$ moles of HRP at 25° C. with 100 μL of a reagent comprising 0.055 M tris buffer, pH 8.6, 0.25 mM urea peroxide, 0.05 mM p-phenylphenol, 0.5 mM EDTA, 0.0125% Tween 20 and $3.3 \times 10^{-4}$ M compound 48.

Reagent compositions comprising 0.055 M tris buffer, pH 8.6, 0.25 mM urea peroxide, 0.05 mM p-phenylphenol, 0.5 mM EDTA, 0.0125% Tween 20 and $3.3\times10^{-4}$ M compound 48 were tested for production of chemiluminescence by reacting a 100 µL aliquot with $3.5\times10^{-15}$ moles of HRP. The chemiluminescence time profile is depicted in FIG. 10.

32. Chemiluminescent Detection of HRP with Compound 49

Figure 11:
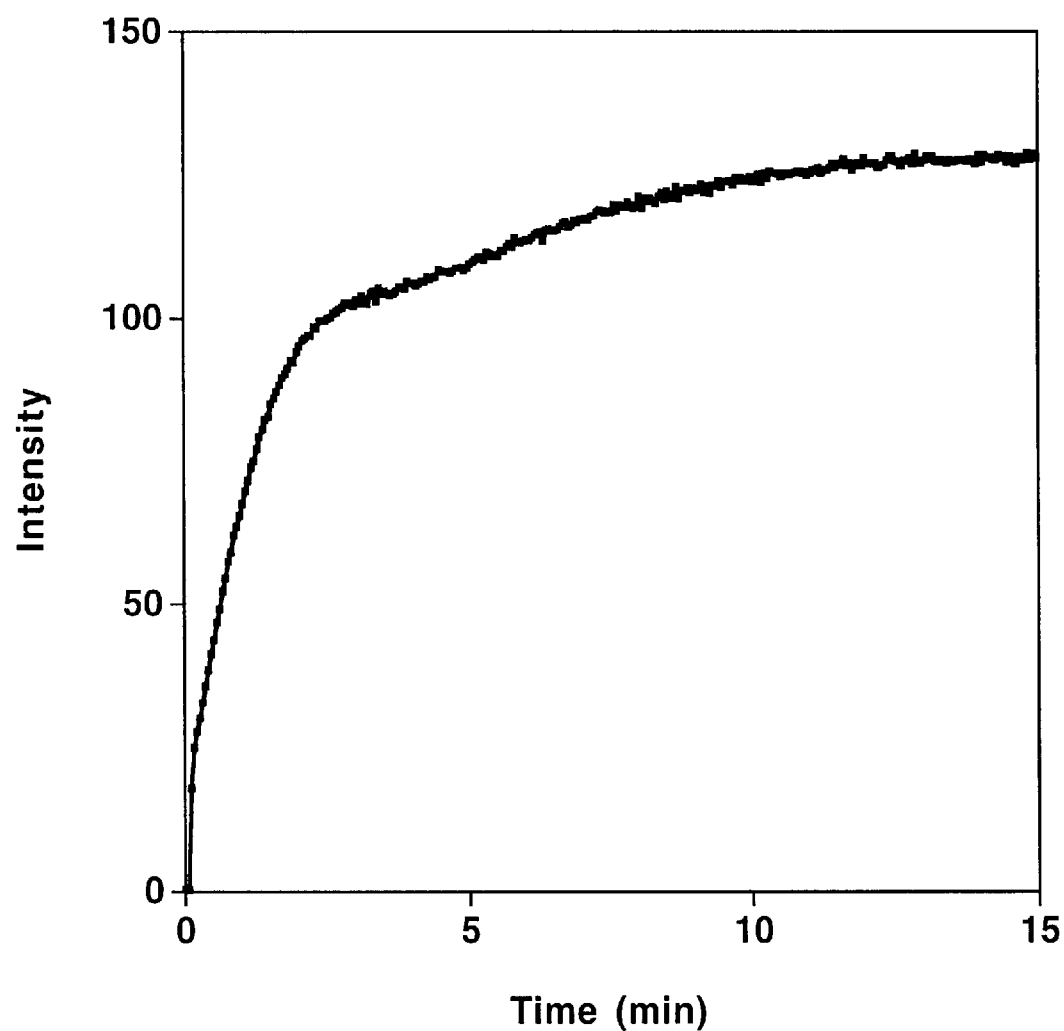
FIG. 11 is a graph showing the time profile of chemiluminescence resulting from reaction of $3.3 \times 10^{-15}$ moles of HRP at 25° C. with 100 μL of a reagent comprising 0.055 M tris buffer, pH 8.6, 0.25 mM urea peroxide, 0.05 mM p-phenylphenol, 0.5 mM EDTA, 0.0125% Tween 20 and $3.3 \times 10^{-4}$ M compound 49.

Reagent compositions comprising 0.055 M tris buffer, pH 8.6, 0.25 mM urea peroxide, 0.05 mM p-phenylphenol, 0.5 mM EDTA, 0.0125% Tween 20 and $3.3\times10^{-4}$ M compound 49 were tested for production of chemiluminescence by reacting a 100 µL aliquot with $3.3\times10^{-15}$ moles of HRP. The chemiluminescence time profile is depicted in FIG. 11.

33. Western Blot Assay using PVDF Membrane

Figure 12:
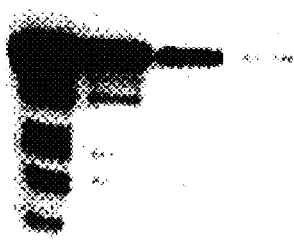
FIG. 12 is an image of an x-ray film from a Western blot assay of β-galactosidase via an HRP-labeled antibody on a PVDF membrane with a chemiluminescent reagent composition. Dilutions of β-galactosidase containing from 5000, 1000, 180, 30 and 5 pg, respectively, of protein were detected with a reagent comprising 0.055 M tris buffer, pH 8.6 containing 0.66 mM acridan phosphate 5, 0.05 mM p-phenylphenol, 0.25 mM urea peroxide, 0.5 mM EDTA, 0.0125% Tween 20 by exposing the membrane to X-ray film for 30 s after a 14 min incubation.

Compositions of the present invention were used to detect and quantify a protein, β-galactosidase (β-gal) in a Western blot with an HRP-labeled antibody on a polyvinylidene difluoride (PVDF) membrane. Dilutions of β-gal containing 5000, 1000, 180, 30 and 5 pg, respectively, of protein were electrophoresed and transferred to PVDF membranes (Millipore, Bedford, Mass.). The membranes were blocked with 1% non-fat milk in T-TBS (0.05% Tween 20 in TBS; TBS is 50 mmol/L Tris-HCl, pH 7.4, 0.15 mol/L NaCl) and then reacted sequentially with a 1:1500 dilution of mouse anti-β-gal (Boehringer-Mannheim, Indianapolis) and 1:600 dilution of sheep anti-mouse-HRP conjugate (Boehringer-Mannheim). The membranes were washed in T-TBS and soaked for 3 min with a reagent comprising 0.055 M tris buffer, pH 8.6 containing 0.66 mM acridan phosphate 5, 0.05 mM p-phenylphenol, 0.25 mM urea peroxide, 0.5 mM EDTA, 0.0125% Tween 20. The membranes were placed between transparent plastic sheets and exposed to X-ray film. FIG. 12 demonstrates the detection of β-gal after 14 min with a 30 s exposure. The light produced led to intense emission which could be imaged for several hours.

34. Western Blot using Nitrocellulose Membrane

Figure 13:
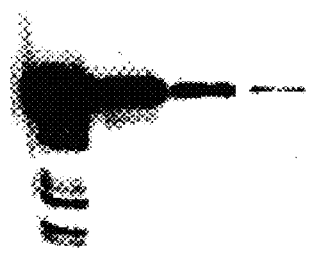
FIG. 13 is an image of an x-ray film from a similar Western blot experiment using a nitrocellulose membrane. The image was obtained by exposing the membrane to x-ray film for 5 min after a 10 min incubation time.

A Western blot assay according to the procedure in the previous example was performed using nitrocellulose membrane (Schleicher & Schuell, Keene, N.H.) as the solid phase. β-Gal standards in the range of 5000–5 pg were used. The detection reagent of the previous example permitted detection to be performed over several hours. FIG. 13 demonstrates the detection of β-gal after 10 min with a 5 min exposure.

35. Western Blot using Other Chemiluminescent Reagents of the Present Invention

Similar Western blot assays of β-galactosidase on both PVDF and nitrocellulose membranes using detection reagents containing in place of compound 5, each of compounds 1, 12 and 13 with qualitatively the same result.

35. Southern Blot using a Chemiluminescent Reagents of the Present Invention

A Southern blot assay can be performed according to the methods described in applicant's U.S. Pat. No. 5,593,845 by substituting for the detection reagent described therein a reagent composition according to Example 20 or 33 of the present invention.

The foregoing description and examples are illustrative only and not to be considered as restrictive. It is recognized that modifications of the specific compounds and methods not specifically disclosed can be made without departing from the spirit and scope of the present invention. The scope of the invention is limited only by the appended claims.

What is claimed is:

1. A compound of the formula III or IV

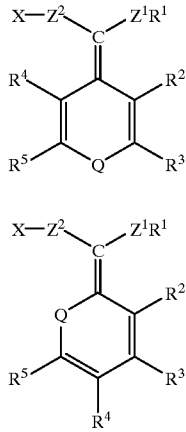

wherein X is selected from substituted or unsubstituted alkyl, substituted or unsubstituted aryl, substituted or unsubstituted aralkyl groups of 1–20 carbon atoms, substituted or unsubstituted alkyl or aryl carboxyl groups having from 1–20 carbon atoms, tri($C_1$–$C_8$ alkyl)silyl groups, a $SO_3$- group and glycosyl groups, Q is selected from $NR^6$, O and S atoms, each of $R^2$ to $R^5$ is a substituent containing from 1 to 50 atoms selected from C, H, N, O, S, P, Si and halogen atoms and wherein pairs of adjacent groups can be joined together to form a carbocyclic or heterocyclic ring system comprising at least one 5 or 6-membered ring and wherein $R^6$ is an organic group containing from 1 to 50 atoms non-hydrogen atoms selected from C, N, O, S, P, Si and halogen atoms provided that $R^6$ is not a trimethylsilyl group, $Z^1$ and $Z^2$ are independently selected from O and S atoms and $R^1$ is an organic group containing from 1 to 50 non-hydrogen atoms selected from C, N, O, S, P, Si and halogen atoms.

2. The compound of claim 1 wherein, in the compound of formula III $Z^2$ is oxygen, Q is the $NR^6$ group and having the formula:

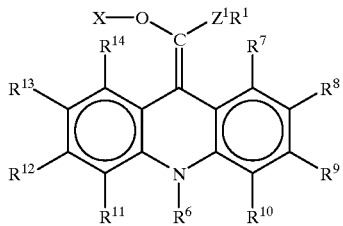

wherein each of to $R_7$ to $R_{14}$ is independently a substituent which can contain from 1 to 50 atoms selected from C, H, N, O, S, P, Si and halogen atoms.

3. The compound of claim 2 wherein at least one of $R_7$ to $R_{14}$ is a halogen or an alkoxy group and the remaining of $R_7$ to $R_{14}$ are hydrogen.

4. The compound of claim 3 wherein $R^6$ is selected from $C_1$–$C_4$ substituted or unsubstituted alkyl, substituted or unsubstituted benzyl, alkoxyalkyl and carboxyalkyl groups.

5. The compound of claim 2 having the formula:

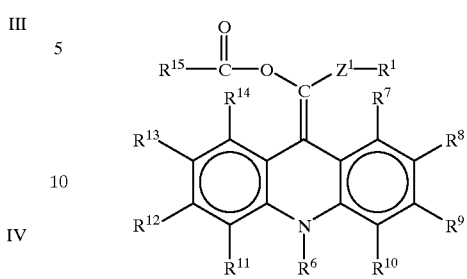

wherein $R^{15}$ is a substituted or unsubstituted alkyl or aryl group having from 1–20 carbon atoms.

6. The compound of claim 5 wherein each of $R^7$ to $R^{14}$ is a hydrogen atom and $R^{15}$ is methyl.

7. The compound of claim 1 wherein, in the compound of formula III, Q is the S atom, and having the formula:

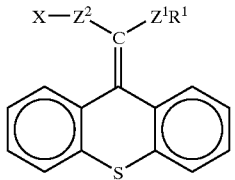

wherein X is selected from substituted or unsubstituted alkyl, substituted or unsubstituted aryl, substituted or unsubstituted aralkyl groups of 1–20 carbon atoms, substituted or unsubstituted alkyl or aryl carboxyl groups having from 1–20 carbon atoms, tri($C_1$–$C_8$ alkyl)silyl groups, an $SO_3^-$ group and glycosyl groups, $Z^1$ and $Z^2$ are independently selected from O and S atoms and $R^1$ is an organic group containing from 1 to 50 non-hydrogen atoms selected from C, N, O, S, P, Si and halogen atoms.

8. The compound of claim 1 wherein, in the compound of formula III, Q is the O atom, and having the formula:

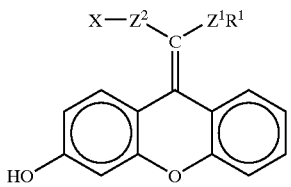

wherein X is selected from substituted or unsubstituted alkyl, substituted or unsubstituted aryl, substituted or unsubstituted aralkyl groups of 1–20 carbon atoms, substituted or unsubstituted alkyl or aryl carboxyl groups having from 1–20 carbon atoms, tri($C_1$–$C_8$ alkyl)silyl groups, an $SO_3$- group and glycosyl groups, $Z^1$ and $Z^2$ are independently selected from O and S atoms and $R^1$ is an organic group containing from 1 to 50 non-hydrogen atoms selected from C, N, O, S, P, Si and halogen atoms.

9. The compound of claim 1 wherein $Z^1$ and $Z^2$ are both sulfur atoms.

* * * * *